United States Patent
Sycheva et al.

(10) Patent No.: US 9,574,216 B2
(45) Date of Patent: Feb. 21, 2017

(54) **AUTO-INDICIBLE EXPRESSION SYSTEM, AND THE USE THEREOF FOR PRODUCING USEFUL METABOLITES USING A BACTERIUM OF THE FAMILY *ENTEROBACTERIACEAE***

(71) Applicant: AJINOMOTO CO., INC., Tokyo (JP)

(72) Inventors: Elena Viktorovna Sycheva, Moscow Region (RU); Valery Vasilievich Samsonov, Moscow Region (RU); Ekaterina Alekseevna Savrasova, Moscow (RU); Natalia Sergeevna Eremina, Moscow (RU); Natalia Vladimirovna Geraskina, Moscow (RU); Natalia Viktorovna Stoynova, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 214 days.

(21) Appl. No.: 14/499,655

(22) Filed: Sep. 29, 2014

(65) Prior Publication Data

US 2015/0017693 A1 Jan. 15, 2015

Related U.S. Application Data

(63) Continuation of application No. PCT/JP2013/060570, filed on Apr. 2, 2013.

(30) Foreign Application Priority Data

Apr. 2, 2012 (RU) ................................ 2012112651

(51) Int. Cl.
*C12P 13/08* (2006.01)
*C12N 15/63* (2006.01)
*C12N 15/70* (2006.01)
*C12P 13/06* (2006.01)

(52) U.S. Cl.
CPC ............... *C12P 13/08* (2013.01); *C12N 15/63* (2013.01); *C12N 15/70* (2013.01); *C12P 13/06* (2013.01)

(58) Field of Classification Search
None
See application file for complete search history.

(56) References Cited

U.S. PATENT DOCUMENTS

| | | | |
|---|---|---|---|
| 4,278,765 A | 7/1981 | Debabov et al. | |
| 4,346,170 A | 8/1982 | Sano et al. | |
| 5,661,012 A | 8/1997 | Sano et al. | |
| 5,965,391 A | 10/1999 | Reinscheid et al. | |
| 5,998,178 A | 12/1999 | Hashiguchi et al. | |
| 6,040,160 A | 3/2000 | Kojima et al. | |
| 7,915,018 B2 | 3/2011 | Rybak et al. | |
| 8,460,903 B2 | 6/2013 | Savrasova et al. | |
| 8,679,798 B2 | 3/2014 | Yampolskaya et al. | |
| 8,728,774 B2 | 5/2014 | Rybak et al. | |
| 2006/0216796 A1 | 9/2006 | Hashiguchi et al. | |
| 2009/0197309 A1 | 8/2009 | Sycheva et al. | |
| 2012/0219996 A1 | 8/2012 | Rybak et al. | |
| 2012/0237986 A1 | 9/2012 | Ziyatdinov et al. | |
| 2013/0224806 A1 | 8/2013 | Savrasova et al. | |
| 2014/0051132 A1 | 2/2014 | Samsonova et al. | |
| 2014/0147909 A1 | 5/2014 | Yampolskaya et al. | |

FOREIGN PATENT DOCUMENTS

| WO | WO2004/065555 | 8/2004 |
|---|---|---|
| WO | WO2010/136897 | 12/2010 |
| WO | WO2013/151174 | 10/2013 |

OTHER PUBLICATIONS

Rhee et al. (Leucine-responsive Regulatory Protein-DNA Interactions in the Leader Region of the ilvGMEDA Operon of *Escherichia coli*, The Journal of Biological Chemistry vol. 271, No. 43, Issue of Oct. 25, pp. 26499-26507, 1996).*
Schell, M. A. et al., "Molecular Biology of the LysR Family of Transcriptional Regulators," Annu. Rev. Microbiol. 1993;47:597-626.
Bansal, K., et al., "A positive feedback-based gene circuit to increase the production of a membrane protein," J. Biol. Eng. 2010;4(6):1-7.
Maddocks, S. E., et al., "Structure and function of the LysR-type transcriptional regulator (LTTR) family proteins," Microbiol. 2008;154:3609-3623.
Nistala, G. J., et al., "A modular positive feedback-based gene amplifier," J. Biol. Eng. 2010;4(4):1-8.
Poellinger, K. A., et al., "Intragenic suppression of a luxR mutation: Characterization of an autoinducer-independent LuxR," FEMS Microbiol. Lett. 1995;129:97-102.
Rhee, K. Y., et al., "Transcriptional coupling between the divergent promoters of a prototypic LysR-type regulatory system, the ilvYC operon of *Escherichia coli*," PNAS 1999;96(25):14294-14299.
Rhee, K. Y., et al., "Activation of Gene Expression by a Ligand-induced Conformational Change of a Protein-DNA Complex," J. Biol. Chem. 1998;273:11257-11266.
Sayut, D. J., et al., "Noise and kinetics of LuxR positive feedback loops," Biochem. Biophys. Res. Comm. 2007;363:667-673.
Wek, R. C., et al., "Nucleotide Sequence and in Vivo Expression of the ilvY and ilvC Genes in *Escherichia coli* K12," J. Biol. Chem. 1986;261(5):2441-2450.

(Continued)

*Primary Examiner* — Suzanne M Noakes
*Assistant Examiner* — Jae W Lee
(74) *Attorney, Agent, or Firm* — Shelly Guest Cermak; Cermak Nakajima & McGowan LLP

(57) ABSTRACT

The present invention describes a method for producing a useful metabolite using a bacterium of the family Enterobacteriaceae, particularly a bacterium belonging to the genus *Escherichia*, which has been modified to contain a gene(s) expression system including elements of the LysR-type protein-regulated transcriptional machinery modified in such a way that auto-inducible positive feedback regulation of the system is mediated by a coinducer. The method is suitable for producing branched-chain L-amino acids, particularly L-valine, L-isoleucine and L-leucine; and D-pantothenic acid.

21 Claims, 1 Drawing Sheet

(56) References Cited

OTHER PUBLICATIONS

International Search Report for PCT Patent App. No. PCT/JP2013/060570 (Jun. 24, 2013).
Written Opinion for PCT Patent App. No. PCT/JP2013/060570 (Jun. 24, 2013).

* cited by examiner

US 9,574,216 B2

AUTO-INDICIBLE EXPRESSION SYSTEM, AND THE USE THEREOF FOR PRODUCING USEFUL METABOLITES USING A BACTERIUM OF THE FAMILY ENTEROBACTERIACEAE

This application is a Continuation of, and claims priority under 35 U.S.C. §120 to, International Application No. PCT/JP2013/060570, filed Apr. 2, 2013, and claims priority therethrough under 35 U.S.C. §119 to Russian Patent Application No. 2012112651, filed Apr. 2, 2012, the entireties of which are incorporated by reference herein. Also, the Sequence Listing filed electronically herewith is hereby incorporated by reference (File name: 2014-09-29T_US-519_Seq_List; File size: 52 KB; Date recorded: Sep. 29, 2014).

BACKGROUND OF THE INVENTION

Field of the Invention

The present invention relates to the microbiological industry, and specifically to a method for producing useful metabolites by fermentation of a bacterium of the family Enterobacteriaceae, wherein the LysR-type protein-regulated expression system of the bacterium has been modified in such a way that functionality of said expression system is mediated by a coinducer, and as a result, the expression levels of the genes regulated by said expression system are enhanced. More specifically, the expression system and the method can be useful for improving the production of metabolites from synthetic pathways of L-amino acids, such as the branched-chain L-amino acid.

Brief Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765) and alteration of regulatory regions such as promoter, leader sequence, and/or attenuator or others known to the person skilled in the art (see, for example, US20060216796 A1 and WO9615246 A1). Other techniques for enhancing production yields include increasing the activities of enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170, 5,661,012, and 6,040,160). For example, the mutant bacterial acetohydroxy-acid synthetase I (also referred to as acetolactate synthase I, hereinafter AHAS I) which is resistant to feedback inhibition by L-valine has been utilized for improving branched-chain L-amino acid production in corresponding L-amino acid producing strains (Russian Patent No. 2355763).

The biosynthesis of branched-chain L-amino acids (BCAAs), such as L-valine, L-leucine, and L-isoleucine, occurs through a branched biosynthetic pathway. Acetolactate synthase (the enzyme classification (EC) number 2.2.1.6) catalyzes the reaction in the first step in the pathway, which is common to all three amino acid's biosynthetic pathways. The reaction includes condensation of activated acetaldehyde (2-(α-hydroxyethyl)thiamine diphosphate) derived from pyruvate with either pyruvate or 2-oxobutanoate to yield 2-acetolactate (AL) or 2-aceto-2-hydroxybutanoate (AHB), respectively. AL is a precursor of L-valine and L-leucine, and AHB is a precursor of L-isoleucine. In *Escherichia coli* (*E. coli*), for example, reactions between pyruvate molecules, as well as reactions between pyruvate and 2-oxobutanoate, are catalyzed by the three AHAS isozymes, AHAS I, AHAS II, and AHAS III, which are encoded by the ilvBN, ilvGM, and ilvIH genes, respectively. AHAS I and AHAS III are the targets for the end-product inhibition (also referred to as feedback inhibition) by L-valine. The feedback inhibition by the end-product plays a major role in the physiological control of these pathways in bacteria.

The products of the AHAS catalyzed reaction, AL or AHB, are the substrates for 2-acetohydroxy acid isomeroreductase IlvC (EC 1.1.1.86) which is encoded by the ilvC gene, a member of the ilvYC operon. The ilvYC operon of *E. coli* is a prototypical LysR protein-regulated system which is the most common type of positive regulatory system in bacteria, and can be found in prokaryotic bacterial families ranging from Enterobacteriaceae to Rhizobiaceae (Rhee K. Y. et al., *Proc. Nat. Acad. Sci. USA,* 1999, 96:14294-14299). The ilvY gene encodes the LysR-type regulatory protein IlvY, a transcriptional regulator, which binds in a highly cooperative fashion to two tandem operator regions in the divergent-overlapping ilvYC promoter region (FIG. 1). Upon binding to the first operator region, the IlvY regulator negatively auto-regulates transcription from the ilvY promoter thus attenuating its own synthesis. Apart from this function, IlvY plays a pivotal role in activation of transcription of the ilvC gene. Activation of ilvC transcription requires binding of the IlvY regulator to the second operator region and additional binding of a coinducer such as 2-acetolactate (AL) or 2-aceto-2-hydroxybutanoate (AHB) to a preformed IlvY/DNA complex. Upon binding a coinducer, a conformational change in the protein/DNA complex occurs that remodels the −35 region of the ilvC promoter and drastically increases RNA polymerase binding capacity (Rhee K. Y. et al., *J. Biol. Chem.,* 1998, 273:11257-11266).

In the L-valine and L-leucine biosynthesis, 2-acetolactate (AL) is converted by the IlvC protein into 2,3-dihydroxy-3-methylbutanoate (also referred to as 2,3-dihydroxy-isovalerate, DHIV) (FIG. 2). In L-isoleucine biosynthesis, 2-aceto-2-hydroxybutanoate (AHB) is converted by IlvC into 2,3-dihydroxy-3-methylpentanoate (also referred to as 2,3-dihydroxy-3-methylvalerate, DHMV).

Recently, auto-inducible gene expression systems were recognized as being very attractive for enhancing expression of a desired gene over routine genetic approaches. For example, the literature provides an artificially designed positive feedback-based gene expression system that can function as a genetic signal amplifier heightening the sensitivity to protein inducer signals as well as increasing maximum expression levels without the need for the external cofactor acyl homoserine lactone (AHL, also abbreviated as HSL) (Nistala G. J. et al., *J. Biol. Eng.,* 2010, 4:4). The designed system utilizes a constitutively active variant of the quorum-sensing (QS) regulator LuxR (lux operon) from *Vibrio fischeri,* which is auto-inducer (AHL)-independent due to the Ala221Val point mutation (Sayut D. J. et al., *Biochem. Biophys. Res. Commun.,* 2007, 363:667-673; Poellinger K. A. et al., *FEMS Microbiol Lett.,* 1995, 129: 97-101). A similar gene expression system with slight variations has been applied to manipulate the expression kinetics of a model membrane protein, cytochrome bd quinol oxidase in *E. coli* (Bansal K. et al., *J. Biol. Eng.,* 2010, 4:6).

The auto-inducible positively feedback regulated activation system based on quorum-sensing machinery from *V. fischery* (lux bioluminescence genes) and an endogenous source of an auto-inducer (HSL) have been utilized for expressing recombinant proteins such as as antigens to prepare pharmaceutical compositions (WO2010136897 A2).

However, no data has been reported to date describing a LysR-type protein-regulated gene(s) expression system modified in such a way that the functionality of said expression system is mediated by a coinducer, and the use thereof for production of useful metabolites from the biosynthetic pathway of L-amino acid such as branched-chain L-amino acids and/or a branched off pathway thereof.

SUMMARY OF THE INVENTION

An aspect of the present invention is to provide a gene(s) expression system that includes elements of the LysR-type protein-regulated transcriptional machinery modified in such a way that auto-inducible positive feedback regulation of the system is mediated by a coinducer.

Another aspect of the present invention is to provide a bacterium of the family Enterobacteriaceae, which may belong to the genus *Escherichia* and, more specifically, to the species *Escherichia coli*, which has been modified to contain the expression system.

Another aspect of the present invention is to provide a method for producing useful metabolites, for example, L-amino acids such as branched-chain L-amino acids, or salts thereof, in particular, L-valine, L-isoleucine, and L-leucine, or salts thereof. This aim was achieved by the finding that modification of genes encoding the mutant acetolactate synthase, which is resistant to the feedback inhibition by L-valine, in such a way that the expression of the genes is regulated by the LysR-type protein-regulated transcriptional machinery, and the expression is further mediated by a coinducer which is produced by the acetolactate synthase reaction results in increased production of branched-chain L-amino acids.

It is an aspect of the present invention to provide a gene expression system comprising the LysR-type protein-regulated transcriptional machinery which comprises a promoter and an operator, the expression of which is positively regulated by the LysR-type regulatory protein and a coinducer, and a gene(s) of interest to which the transcriptional machinery is operably linked, wherein the gene(s) of interest encode(s) a protein(s) involved in biosynthesis of the coinducer, a substrate, or a precursor of the coinducer, whereby auto-inducible positive feedback regulation of the expression system is mediated by the coinducer.

It is a further aspect of the present invention to provide the expression system as described above, wherein the system is from a bacterium belonging to the family Enterobacteriaceae or Pseudomonadaceae.

It is a further aspect of the present invention to provide the expression system as described above, wherein the system is from a bacterium belonging to the family Enterobacteriaceae.

It is a further aspect of the present invention to provide the expression system as described above, wherein the system is from a bacterium belonging to the genus *Escherichia*.

It is a further aspect of the present invention to provide the expression system as described above, wherein the bacterium belongs to the species *Escherichia coli*.

It is a further aspect of the present invention to provide the expression system as described above, wherein the system is from the biosynthetic pathway of L-amino acid selected from the group consisting of branched-chain L-amino acids, L-lysine, L-cystein, L-methionine, and L-tryptophan.

It is a further aspect of the present invention to provide the expression system as described above, wherein the system is from the branched-chain L-amino acids biosynthetic pathway.

It is a further aspect of the present invention to provide the expression system as described above, wherein the promoter is the $P_{ilvC}$ promoter, the LysR-type regulatory protein is the IlvY protein, and the coinducer is 2-acetolactatic acid, 2-aceto-2-hydroxybutyric acid or salts thereof.

It is a further aspect of the present invention to provide the expression system as described above, wherein the coinducer is 2-acetolactic acid or a salt thereof.

It is a further aspect of the present invention to provide the expression system as described above, wherein the gene(s) of interest encode(s) acetohydroxy-acid synthetase.

It is a further aspect of the present invention to provide the expression system as described above, wherein the genes of interest encode proteins selected from the group consisting of:

(A) a combination of A1 and A2:
(A1) a protein comprising the amino acid sequences of SEQ ID NO: 2, or a protein comprising the amino acid sequences of SEQ ID NO: 2, but which includes substitution, deletion, insertion, or addition of one or several amino acid residues and has acetolactate synthase activity when in the presence of a protein of A2;
(A2) a protein comprising the amino acid sequence of SEQ ID NO: 4; or a protein comprising the amino acid sequence of SEQ ID NO: 4, but which includes substitution, deletion, insertion, or addition of one or several amino acid residues and has acetolactate synthase activity when in the presence of a protein of A1;
(B) a combination B1 and B2:
(B1) a protein comprising the amino acid sequence of SEQ ID NO: 6; or a protein comprising the amino acid sequence of SEQ ID NO: 6, but which includes substitution, deletion, insertion, or addition of one or several amino acid residues and has acetolactate synthase activity when in the presence of a protein of B2;
(B2) a protein comprising the amino acid sequence of SEQ ID NO: 8; or a protein comprising the amino acid sequence of SEQ ID NO: 8, but which includes substitution, deletion, insertion, or addition of one or several amino acid residues and has acetolactate synthase activity when in the presence of a protein of B1; and
(C) a combination of C1 and C2:
(C1) a protein comprising the amino acid sequence of SEQ ID NO: 32; or a protein comprising the amino acid sequence of SEQ ID NO: 32, but which includes substitution, deletion, insertion, or addition of one or several amino acid residues and has acetolactate synthase activity when in the presence of a protein of C2;
(C2) a protein comprising the amino acid sequence of SEQ ID NO: 34; or a protein comprising the amino acid sequence of SEQ ID NO: 34, but which includes substitution, deletion, insertion, or addition of one or several amino acid residues and has acetolactate synthase activity when in the presence of a protein of C1.

It is a further aspect of the present invention to provide the expression system as described above, wherein the acetohydroxy-acid synthetase is a mutant acetolactate synthase I resistant to feedback inhibition by L-valine.

It is a further aspect of the present invention to provide the expression system as described above, wherein the operator comprises a region to which the LysR-type regulatory protein binds.

It is a further aspect of the present invention to provide the expression system as described above, wherein the LysR-type regulatory protein is selected from the group consisting of:

(D) a protein comprising the amino acid sequence of SEQ ID NO: 10; and
(E) a protein comprising the amino acid sequence of SEQ ID NO: 10, but which includes substitution, deletion, insertion, or addition of one or several amino acid residues and has LysR-type regulatory protein activity.

It is a further aspect of the present invention to provide the expression system as described above, wherein the promoter comprises:

(F) a DNA comprising the nucleotide sequence of SEQ ID NO: 30; or
(G) a DNA comprising the nucleotide sequence of SEQ ID NO: 30, but which includes substitution, deletion, insertion, or addition of one or several nucleotide residues and has activity of the nucleotide sequence of SEQ ID NO: 30.

It is an aspect of the present invention to provide an L-amino acid-producing bacterium belonging to the family Enterobacteriaceae, wherein the bacterium has been modified to contain the expression system as described above.

It is a further aspect of the present invention to provide the bacterium as described above, wherein the bacterium contains a gene encoding the LysR-type regulatory protein.

It is a further aspect of the present invention to provide the bacterium as described above, wherein the bacterium belongs to the genus *Escherichia*.

It is a further aspect of the present invention to provide the bacterium as described above, wherein the bacterium belongs to the species *Escherichia coli*.

It is a further aspect of the present invention to provide the bacterium as described above, wherein the L-amino acid is branched-chain L-amino acid.

It is a further aspect of the present invention to provide the bacterium as described above, wherein the branched-chain L-amino acid is selected from the group consisting of L-valine, L-leucine, and L-isoleucine.

It is an aspect of the present invention to provide a method for producing a branched-chain L-amino acid comprising:
(i) cultivating the bacterium as described above in a culture medium so that the branched-chain L-amino acid is accumulated in the culture medium; and
(ii) collecting the branched-chain L-amino acid from the culture medium.

It is a further aspect of the present invention to provide the method for producing the branched-chain L-amino acid as described above, wherein the branched-chain L-amino acid is selected from the group consisting of L-valine, L-leucine, and L-isoleucine.

BRIEF DESCRIPTION OF THE DRAWINGS

Minus sign (−) means negative influence on gene transcription.
Plus sign (+) means positive influence on gene transcription.

DESCRIPTION OF THE PREFERRED EMBODIMENTS

Figure 1:
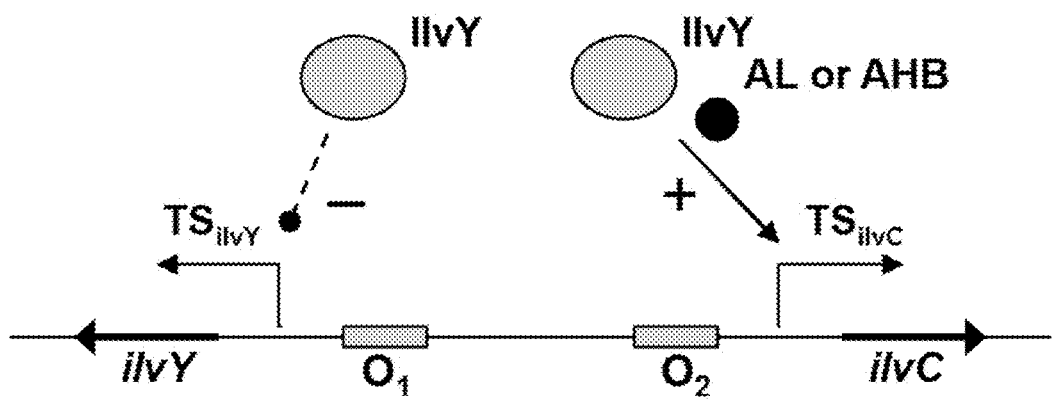
FIG. 1 shows the scheme for regulation of transcription of the ilvY and ilvC genes.
IlvY is the LysR-type transcriptional regulator.
AL or AHB is coinducer 2-acetolactate or 2-aceto-2-hydroxybutanoate.
O1 and O2 are operator regions 1 and 2.
$TS_{ilvC}$ means the transcription start of the ilvC gene.
$TS_{ilvY}$ means the transcription start of the ilvY gene.
Figure 2:
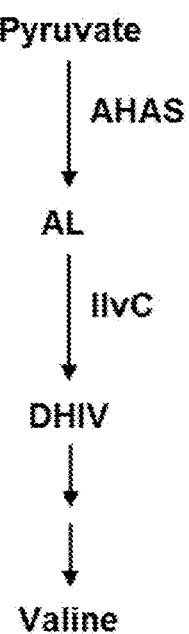
FIG. 2 shows the scheme for biosynthesis of L-valine from pyruvate.
AL is 2-acetolactate.
DHIV is 2,3-dihydroxy-isovalerate.
AHAS is acetolactate synthase.
IlvC is isomeroreductase.

The present invention is described in detail below.
1. Bacterium
The phrase "useful metabolite" is not particularly limited so long as the metabolite can be produced by an enzymatic reaction or biosynthetic pathway, and can include L-amino acids, higher alcohols, and D-pantothenic acid.

The phrase "an L-amino acid-producing bacterium" can mean a bacterium of the family Enterobacteriaceae which has an ability to produce and cause accumulation of an L-amino acid in a culture medium when the bacterium is cultured in the medium. The L-amino acid-producing ability can mean the ability of the bacterium to produce an L-amino acid in a medium or the bacterial cells and cause accumulation of the L-amino acid to such an extent that the L-amino acid can be collected from the medium or the bacterial cells, when the bacterium is cultured in the medium.

The phrase "L-amino acid" can include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

The phrase "branched L-amino acid" can include L-valine, L-leucine, and L-isoleucine.

The bacterium may inherently have the ability to produce the useful metabolite such as an L-amino acid or may be modified to have such an ability by using a mutation method or DNA recombination techniques.

The bacteria belonging to the family Enterobacteriaceae can be from the genera *Enterobacter, Erwinia, Escherichia, Klebsiella, Morganella, Pantoea, Photorhabdus, Providencia, Salmonella, Yersinia*, and so forth, and can have the ability to produce an L-amino acid. Specifically, those classified into the family Enterobacteriaceae according to the taxonomy used in the NCBI (National Center for Biotechnology Information) database (www.ncbi.nlm.nih.gov/Taxonomy/Browser/wwwtax.cgi?id=543) can be used. Examples of strains from the family Enterobacteriaceae which can be modified include a bacterium of the genus *Escherichia, Enterobacter*, or *Pantoea*.

Strains of *Escherichia* bacterium which can be modified to obtain *Escherichia* bacteria in accordance with the presently disclosed subject matter are not particularly limited, and specifically, those described in the work of Neidhardt et al. can be used (Bachmann, B. J., Derivations and genotypes of some mutant derivatives of *E. coli* K-12, p. 2460-2488. In F. C. Neidhardt et al. (ed.), *E. coli* and *Salmonella*: cellular and molecular biology, $2^{nd}$ ed. ASM Press, Washington, D.C., 1996). The species *E. coli* is a particular example. Specific examples of *E. coli* include *E. coli* W3110 (ATCC 27325), *E. coli* MG1655 (ATCC 47076), and so forth, which are derived from the prototype wild-type strain, K-12 strain. These strains are available from, for example, the American Type Culture Collection (P.O. Box 1549, Manassas, Va. 20108, United States of America). That is, registration numbers are given to each of the strains, and the strains can be ordered by using these registration numbers (refer to www.atcc.org). The registration numbers of the strains are listed in the catalogue of the American Type Culture Collection.

Examples of the *Enterobacter* bacteria include *Enterobacter agglomerans, Enterobacter aerogenes*, and so forth. Examples of the *Pantoea* bacteria include *Pantoea ananatis*, and so forth. Some strains of *Enterobacter agglomerans* were recently reclassified into *Pantoea agglomerans, Pantoea ananatis* or *Pantoea stewartii* on the basis of nucleotide sequence analysis of 16S rRNA, etc. A bacterium belonging to any of the genus *Enterobacter* or *Pantoea* may be used so long as it is a bacterium classified into the family Enterobacteriaceae. When a *Pantoea ananatis* strain is bred by genetic engineering techniques, *Pantoea ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

Examples of the bacterium belonging to the family Pseudomonadaceae can be from the genus *Pseudomonas*. Examples of the *Pseudomonas* bacteria include *Pseudomonas putida, P. aeruginosa*, and *P. syringae*.

The phrase "a bacterium which has been modified to contain the expression system" can mean a bacterium, for example, an L-amino acid-producing bacterium of the family Enterobacteriaceae, wherein a LysR-type protein-regulated expression system has been modified in such a way that the functionality of auto-inducible positive feedback regulation of said system is mediated by a coinducer. For example, the phrase "a bacterium which has been modified to contain the expression system" can mean a bacterium of the family Enterobacteriaceae having an ability to produce L-amino acid such as branched-chain L-amino acid, which has been modified to have the gene(s) expression system.

Branched-Chain L-Amino Acid-Producing Bacterium

The phrase "a branched-chain L-amino acid-producing bacterium" can mean a bacterium which has an ability to produce and cause accumulation of branched-chain L-amino acids in a medium such as L-valine, L-leucine and L-isoleucine, when the bacterium is cultured in the medium. The branched-chain L-amino acids, apart from L-valine, L-leucine and L-isoleucine, may also include unnatural branched-chain L-amino acids such as L-homoleucine and L-homoisoleucine. The branched-chain L-amino acid producing ability may be imparted or enhanced by breeding. The phrase "a branched-chain L-amino acid-producing bacterium" can indicate also a bacterium which is able to produce and cause accumulation of branched-chain L-amino acids in a culture medium in an amount larger than a non-modified strain, for example, a wild-type or a parent strain, and can also mean that the bacterium is able to produce and cause accumulation in a medium of the branched-chain L-amino acids in an amount of not less than 0.5 g/L, or even not less than 1.0 g/L.

The branched-chain L-amino acid-producing bacterium can be a bacterium of the family Enterobacteriaceae, which contains a regulatory region which positively affects expression of the acetolactate synthase genes by a complex which includes a transcription regulatory protein and a coinducer which is a product of acetolactate synthase catalyzed reaction. Furthermore, the bacterium can be a branched-chain L-amino acid-producing bacterium of the family Enterobacteriaceae which has increased mutant acetolactate synthase activity. Specifically, the bacterium can be a branched-chain L-amino acid-producing bacterium of the family Enterobacteriaceae, wherein branched-chain L-amino acid production by the bacterium is increased by enhancing activity of the mutant acetolactate synthase by introducing the regulatory region into the bacterium. The bacterium is a branched-chain L-amino acid-producing bacterium belonging to the genus *Escherichia*, wherein branched-chain L-amino acid production by the bacterium can be increased by enhancing activity of the mutant acetolactate synthase resistant to the feedback inhibition by L-valine.

The branched-chain L-amino acid-producing bacterium of the family Enterobacteriaceae is not limited to the bacterium as disclosed above. More specifically, the branched-chain L-amino acid-producing bacterium also can be a L-valine, L-leucine, and/or L-isoleucine-producing bacteria.

L-Valine-Producing Bacteria

Examples of parent strains for deriving L-valine-producing bacteria can include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by L-valine that is produced. Furthermore, the ilvA gene in the operon is desirably disrupted so that threonine deaminase activity is decreased.

Examples of parent strains for deriving L-valine-producing bacteria can include also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russian Federation, 117545 Moscow, $1^{st}$ Dorozhny Proezd, 1) on Jun. 24, 1988 under accession number VKPM B-4411. Furthermore, mutants requiring lipoic acid for growth and/or lacking $H^+$-ATPase can also be used as parent strains (WO96/06926).

As the parent strain, L-valine producing bacteria belonging to the genus *Escherichia* such as H-81 (VKPM B-8066), NRRL B-12287 and NRRL B-12288 (U.S. Pat. No. 4,391, 907), VKPM B-4411 (U.S. Pat. No. 5,658,766), VKPM B-7707 (European Patent Application EP1016710A2), NS1610 (refer to the Patent EP1942183, Example 7 and the examples mentioned herein) or the like can be employed.

L-Leucine-Producing Bacteria

Examples of parent strains for deriving L-leucine-producing bacteria can include, but are not limited to strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5, 5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium can be improved by enhancing the expression of one or more genes involved in L-leucine biosynthesis. Examples include genes of the leuABCD operon, which can be represented by a mutant leuA gene encoding isopropylmalate synthase not subjected to feedback inhibition by L-leucine (U.S. Pat. No. 6,403,342). In addition, the bacterium can be improved by enhancing the expression of one or more genes coding for proteins which excrete L-amino acid from the bacterial cell. Examples of such genes include the b2682 and b2683 genes (ygaZH genes) (EP1239041 A2).

As the parent strain, L-leucine producing bacteria belonging to the genus *Escherichia* such as H-9070 (FERM BP-4704) and H-9072 (FERM BP-4706) (U.S. Pat. No. 5,744,331), VKPM B-7386 and VKPM B-7388 (RU2140450), W1485atpA401/pMWdAR6, W1485lip2/pMWdAR6 and AJ12631/pMWdAR6 (EP0872547), or the like can be employed.

L-Isoleucine-Producing Bacteria

Examples of parent strains for deriving L-isoleucine producing bacteria can include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

As the parent strain, L-isoleucine producing bacteria belonging to the genus *Escherichia* such as strain (NZ10) TDH6/pVIC40, pMWD5 (Hashiguchi K. et al, *Biosci. Biotechnol. Biochem.*, 1999, 63(4):672-679) or strain AJ12919 described in European Patent Application EP685555 A1, or the like can be employed.

Higher Alcohols and D-Pantothenic Acid-Producing Bacteria

The L-amino acids-producing bacterium of the family Enterobacteriaceae, and more specifically the branched-chain L-amino acids producing bacterium of the family Enterobacteriaceae can be used for production of higher alcohols and organic acids, or their derivatives. For example, higher alcohols such as isobutanol, 2-methyl-1-butanol, and 3-methyl-1-butanol; and organic acid such as D-pantothenic acid (vitamin B5) may be produced using such a bacterium.

It is known in the art that in bacteria of the family Enterobacteriaceae, the biosynthetic pathway for L-valine, L-leucine, and L-isoleucine proceeds through keto-acid intermediates. More specifically, 2-oxoisovalerate (2-ketoisovalerate, 2-KIV) is a precursor for L-valine and L-leucine; and 2-oxobutanoate is a precursor for L-isoleucine. Also, it is known in the art that keto-acid intermediates or their derivatives can be the precursors for higher alcohols with a carbon chain of the length more than two atoms due to Ehrlich degradation pathway (Yan Y. and Liao J. C. *J. Ind. Microbiol. Biotechnol.*, 2009, 36:471-479). For example, 2-oxoisovalerate is a precursor for isobutanol, and its derivative 4-methyl-2-oxopentanoate is a precursor for 3-methyl-1-butanol; 2-oxobutanoate is a precursor for n-propanol, and its derivative 3-methyl-2-oxopentanoate is a precursor for 2-methyl-1-butanol.

The ability to produce higher alcohols can be impaired to *E. coli* strains which do not have a native ability to produce higher alcohols by introducing broad-substrate-range keto-acid decarboxylase (KDC) and alcohol dehydrogenase (ADH) encoding genes (kivd and adh2) from host microorganisms. For example, the kivd gene from *Bacillus subtilis* and the adh2 gene from *Lactococcus lactis* may be used. In this aspect, the references may be given to Connor M. R. and Liao J. C., *Appl. Env. Mocrobiol.*, 2008, 74:5769-5775; and Patent Application WO2009046370 A2.

Thus, by introducing into an L-amino acid-producing bacterium of the family Enterobacteriaceae the gene(s) expression system and suitable heterologous genes, for example, kivd and adh2, or their variants, from host microorganisms, the ability to produce higher alcohols such as isobutanol, 3-methyl-1-butanol, and 2-methyl-1-butanol can be imparted to the bacterium.

It is also known in the art that in a bacterium of the family Enterobacteriaceae 2-oxoisovalerate is a precursor for D-pantothenic acid. Thus, by modifying a bacterium of the family Enterobacteriaceae with the gene(s) expression system the ability to produce D-pantothenic acid can be imparted to the bacterium.

2. Expression System

The expression system can be a gene(s) transcription regulatory system which includes elements of the LysR-type protein-regulated transcriptional machinery. The elements of the LysR-type protein-regulated transcriptional machinery can include a promoter and/or an operator. The expression of the transcriptional machinery can be positively regulated by the LysR-type regulatory protein and a coinducer.

The expression system can further include a gene(s) of interest to which above-mentioned transcriptional machinery is operably linked. The phrase "operably linked" can mean that the gene of interest is linked to the regulatory sequence(s) such as a promoter and operator in a manner that allows for expression of the gene.

The gene(s) of interest can encode a protein(s) involved in biosynthesis of the coinducer, a substrate, or a precursor of said coinducer.

According to the above-described design of the expression system, expression of the system can be auto-inducibly and positively feedback-regulated by mediation of the coinducer produced with involvement of expression product(s) of the gene(s) of interest. Such an expression system can be called "the auto-inducible positively feedback regulated expression system", but for reasons of simplicity, may also be referred to as the expression system. The expression system can be positively feedback auto-regulated by a coinducer which may be a substrate or a precursor for a useful metabolite in a biosynthetic pathway, more specifically in the branched-chain L-amino acids biosynthetic pathway and/or a pathway that branches off such a pathway.

The "LysR-type regulatory protein" may also be referred to as the "LysR-type transcriptional regulator (LTTR)", LysR family transcriptional regulator, or simply "regulator". The LysR-type regulatory protein may belong to the diverse family of oligomeric bacterial transcriptional factors which regulate a wide variety of transcription units in response to a wide variety of environmental signals. Members of this family may act as transcriptional activators and/or transcriptional repressors and have several common structural features such as: i) a DNA-binding domain employing a helix-turn-helix motif (residues can be from positions 1 to 65 from the N-terminus of the LTTR), (ii) domains involved in coinducer recognition and/or response (residues can be from 100 to 173 and from 196 to 206), and (iii) a domain required for DNA binding and coinducer response (residues can be from 227 to 253) as described in Schell M. A., *Ann. Rev. Microbiol.*, 1993, 47:597-626. In the absence of a coinducer, LTTRs may bind to regulated promoters via a 15-bp dyadic region with a common structure and position (near −65) as described in Schell M. A., *Ann. Rev. Microbiol.*, 1993, 47:597-626. In the presence of a coinducer, additional interactions of LTTRs with regions near the −35 RNA polymerase binding site and/or DNA bending may occur resulting in transcription activation (Schell M. A., *Ann. Rev. Microbiol.*, 1993, 47:597-626). In addition, some members of the LysR-type regulatory protein family may have four other functional characteristics such as: (i) be coinducer-responsive transcriptional regulator proteins of varying size, such as ranging from 276 to 324 amino acid residues, (ii) independent of the presence of a coinducer, bind at regulated targets to operator DNA regions that have a similar position and structural motif, (iii) be divergently transcribed from a promoter that is very close to or overlaps a promoter of a regulated gene of interest, and (iv) repress their own transcription by a variable extent, such as by 3- to 10-fold, i.e. be negatively auto-regulated as described in Schell M. A., *Ann. Rev. Microbiol.*, 1993, 47:597-626.

For example, but not limited to, the expression system can include the LysR-type protein-regulated transcriptional machinery which contains an auto-inducible positively feedback regulated promoter and operator, and gene(s) of interest. The expression of the system is positively regulated by the LysR-type regulatory protein and a coinducer. Examples of an auto-inducible positively feedback regulated can include the $P_{ilvC}$ promotor. Examples of the LysR-type regulatory protein can include the IlvY protein. Examples of a coinducer can include a member of 2-aceto-2-hydroxycarboxylic acids such as 2-acetolactic acid (AL), 2-aceto-2-hydroxybutyric acid (AHB, also referred to as 2-aceto-2-hydroxybutanoic acid) and a salt thereof. Examples of the gene(s) of interest can include the genes encoding acetolactate synthase I, II and/or III, or mutant variants thereof. An exemplary expression system can be described schematically without limiting the type, amount, and arrangement of elements of the expression system.

The ilvY and ilvC genes are located side by side and transcribed in the opposite direction as illustrated in FIG. 1. Transcription of the ilvY and ilvC genes are initiated by the divergent-overlapping promoters ilvY and ilvC, respectively. However, the words "ilvC promoter" or the "$P_{ilvC}$ promoter" can inclusively mean the ilvY and ilvC promoters. There are two tandem operators in the promoter region (FIG. 1).

The gene(s) of interest is operably linked to the transcriptional machinery, specifically, to the promoter. For example, when the genes of interest are the ilvBN genes encoding acetolactate synthase I, and the promoter is the ilvC promoter, the native promoter region located upstream to the ilvBN genes is replaced by a DNA fragment that includes an inducible promoter of the ilvC gene and the second operator region in such a way that the expression of the genes is controlled by the promoter. For example, the genes on the ilvBN4 operon encoding AHAS I which is resistant to feedback inhibition by L-valine were placed under the ilvC promoter, which becomes transcriptionally activated only when the complex between AL or AHB, the transcriptional regulator IlvY, and the second operator region is formed. The expression cassette which includes the $P_{ilvC}$ promoter and ilvBN4 operon genes allows the ilvBN4 genes to be transcribed to produce AHAS I. The AHAS convertes two moles of pyruvate into one mole of 2-acetolactate (AL), or one mole of pyruvate and one mole of 2-oxobutanoate into one mole of 2-aceto-2-hydroxybutanoate (AHB), depending on the presence of 2-oxobutanoate.

As an advantage of the present invention, a portion of the AHAS I catalyzed reaction product (AL or AHB) acts as a coinducer and binds to the IlvY/DNA complex, inducing transcription of the ilvBN4 operon genes and thus providing synthesis of AL or AHB. Another portion of AL or AHB can be converted into an end-product the branched L-amino acid (L-valine, L-leucine or L-isoleucine) by the ketol-acid reductoisomerase IlvC and other enzymes of the branched L-amino acids biosynthetic pathway as described above.

Continuously supplying the expression system with 2-acetolactate or 2-aceto-2-hydroxybutanoate may account for its auto-inducible properties; and repeatable circuits through the auto-inducible positively feedback regulated expression system may result in a continuous supply of the branched-chain L-amino acid biosynthetic pathways with precursors such as 3-hydroxy-3-methyl-2-oxobutanoate for L-valine and L-leucine or 3-hydroxy-3-methyl-2-oxopentanoate for L-isoleucine.

The proposed approach for gene expression can be referred to as an auto-inducible gene expression system having the positive feedback regulation mediated by the coinducer AL or AHB.

The auto-inducible positively feedback regulated expression system is not limited to the aforementioned expression system including the IlvY transcriptional regulator. Other expression systems using LysR-type regulatory proteins may also be included, examples of which are described in Table 1.

TABLE 1

LysR-type regulatory proteins.

| Organism | Regulatory protein | Coinducer | KEGG entry No. | Pathway |
| --- | --- | --- | --- | --- |
| E. coli | IlvY | 2-Acetolactate, 2-Aceto-2-hydroxybutanoate | B3773 | Valine, leucine, isoleucine biosynthesis |
| E. coli | LysR | Diaminopimelic acid | B2839 | Lysine biosynthesis |
| E. coli, Salmonella typhimurium | CysB | O-Acetyl-L-serine, N-Acetyl-L-serine | B1275, STM1713 | Cysteine biosynthesis |
| E. coli, S. typhimurium | MetR | L-Homocysteine | B3828, STM3964 | Methionine biosynthesis |
| Pseudomonas putida, P. aeruginosa, P. syringae | TrpI | Indoleglycerol-phosphate | PP_0084, PA0037, PSPTO_0157 | Tryptophan biosynthesis |

The phrase "acetolactate synthase" can mean an enzyme existing in bacterium such as bacteria of the family Enterobacteriaceae, coryneform bacteria, and bacteria belonging to the genus *Bacillus*, etc. The family Enterobacteriaceae may be exemplified by the bacteria belonging to the genera *Escherichia, Pantoea, Erwinia, Providencia*, and *Serratia* such as *E. coli, Pantoea ananatis* (*P. ananatis*), and the like. The coryneform bacteria may be exemplified by the bacteria belonging to the genus *Corynebacterium* such as *Coryne-* bacterium glutamicum. The bacteria belonging to the genus Bacillus may be exemplified by Bacillus subtilis, Bacillus amyloliquefaciens FZB42, and Bacillus amyloliquefaciens DSM7. The acetolactate synthase can also mean an enzyme having activity of acetolactate synthase.

The phrase "activity of acetolactate synthase" can mean an activity of catalyzing the reaction of formation of i) 2-acetolactate and $CO_2$ from two molecules of pyruvate, and/or ii) 2-aceto-2-hydroxybutanoate and $CO_2$ from pyruvate and 2-oxobutanoate under appropriate conditions such as temperature, ionic strength, acidity (pH), cofactors and substrates concentration, and so forth. The acetolactate synthase activity can be measured using the method of Stormer F. C. and Umbarger H. E., Biochem. Biophys. Res. Commun., 1964, 17(5):587-592.

Acetolactate synthase I, II, or III (AHAS I, AHAS II, or AHAS III) (EC 2.2.1.6) can also be referred to as acetolactate synthase. Acetolactate synthase is a heterotetramer protein of $\alpha_2\beta_2$-type structure consisting of two catalytic and two regulatory domains (Weinstock O. et al., J. Bacteriol., 1992, 174(17):5560-5566). It is generally accepted that the large (ca.60-kDa) subunits are catalytic, while the small ones (ca.11-kDa) are regulatory.

AHAS I is encoded by the ilvB and ilvN genes found on the ilvBN operon. AHAS II is encoded by the ilvG and ilvM genes found on the ilvGMEDA operon. AHAS II is not normally expressed in E. coli K-12 cells (Guardiola J. et al., Mol. Gen. Genet., 1977, 156:17-25). AHAS III is encoded by the ilvI and ilvH genes found on the ilvIH operon.

The E. coli AHAS I, for example, can have amino acid residues substitutions such as N17K and/or A30P, which render it resistant to feedback inhibition by L-valine (Russian Patent No. 2355763, U.S. Patent Application No. 2009197309 A1). Also, replacing alanine at position 33 with any amino acid(s), such as replacing it with 12 amino acids containing a translation termination site results in a 45 amino acid truncated protein IlvN33 (Russian Patent No. 2355763, U.S. Patent Application No. 2009197309 A1). This mutant protein is also resistant to feedback inhibition by L-valine.

The mutant AHAS I small subunit having substitution N17K (Asn at position 17 is replaced with Lys, i.e. corresponding codon AAC is replaced with AAG) in the wild-type AHAS I can be encoded by the mutant ilvN gene, which can be referred to as ilvN4 or ilvN ValR4 gene as described in EP1942183. AHAS I having the amino acid sequence of SEQ ID NOs: 2 and 4 may be referred to as "a wild-type acetolactate synthase I"

On the basis of a model of the valine-binding region of the AHAS III regulatory small subunit from E. coli, truncations from the carboxyl-end of the small subunit were made. These truncations induced a lack of valine sensitivity in the truncated AHAS III enzymes (Mendel S. et al., J. Mol. Biol., 2003, 325(2):275-284).

The acetolactate synthase III which is truncated at the carboxyl-end of the small subunit by 35, 48, 80 or 95 amino acid residues may be referred to as the "mutant acetolactate synthase III". A DNA encoding the mutant AHAS III small subunit may be referred to as the "mutant ilvH gene". The ilvIH operon comprising the mutant ilvH gene may be referred to as the "mutant ilvIH operon". AHAS III having the amino acid sequence of SEQ ID NOs: 6 and 8 may be referred to as "a wild-type acetolactate synthase III".

The mutant AHAS I may include deletion, substitution, insertion, or addition of one or several amino acid residues at one or more positions other than 17, 30 and/or 33 in the initial amino acid sequence, provided that the activity of acetolactate synthase is still maintained. Similarly, the mutant AHAS III may also include deletion, substitution, insertion, or addition of one or several amino acid residues at one or more positions in the initial amino acid sequence, provided that the activity of acetolactate synthase is still maintained. Furthermore, the carboxyl-end of the mutant AHAS III can be truncated by one or more amino acid residues, not necessary being restricted to 35, 48, 80 or 95 amino acid residues, as long as activity of acetolactate synthase is not diminished.

The number of "several" amino acid residues differs depending on the position in the three dimensional structure of the protein or the type of amino acid residue. This is because some amino acids are similar to one another in their structure and function within a protein, and interchanging of such amino acids does not greatly affect the three dimensional structure or the function of the protein. The AHAS III can be truncated by an amino acid residues sequence of varying length as long as the truncated construct binds and activates the catalytic (large) subunit so that the mutant AHAS III maintains activity. Therefore, the mutant AHAS I, II and III may be one which has homology of not less than 65%, not less than 80%, not less than 90%, not less than 95%, not less than 97%, not less than 98%, or not less than 99% with respect to the entire amino acid sequence for acetolactate synthase, and as long as the activity of the acetolactate synthase is maintained. In this specification, the term "homology" can mean "identity".

The mutant AHAS I can be obtained by introducing mutations into a wild-type ilvN gene using known methods. For example, the mutant ilvBN4 operon which contains the ilvB and mutant ilvN4 gene can be obtained by PCR (polymerase chain reaction; refer to White T. J. et al., Trends Genet., 1989, 5:185-189) utilizing primers based on the nucleotide sequence of the ilvN gene (SEQ ID NO: 3). Genes coding for acetolactate synthase from other microorganisms can be obtained in a similar manner.

The mutant AHAS III with a truncated carboxyl-end of the small subunit can be obtained by site-directed mutagenesis using overlap extension PCR by placing stop codons to be introduced at desired position of the ilvH gene (Ho S. N. et al., Site-directed mutagenesis by overlap extension using the polymerase chain reaction, Gene, 1989, 77:51-59). The primers for PCR suitable for the ilvIH operon genes synthesis can be chosen by referring to the nucleotide sequence of the ilvH gene (SEQ ID NO: 7).

The ilvB gene encodes the acetolactate synthase I large subunit (KEGG, Kyoto Encyclopedia of Genes and Genomes, entry No. b3671). The ilvB gene (GenBank accession No. NC_000913.2; nucleotide positions: 3849119 to 3850807, complement; Gene ID: 948182) is located between the ilvN and ivbL genes on the chromosome of E. coli K-12. The nucleotide sequence of the ilvB gene and the amino acid sequence of the acetolactate synthase I large subunit encoded by the ilvB gene are shown in SEQ ID NO: 1 and SEQ ID NO: 2, respectively.

The ilvN gene encodes the acetolactate synthase I small subunit (KEGG entry No. b3670). The ilvN gene (GenBank accession No. NC_000913.2; nucleotide positions: 3848825 to 3849115, complement; Gene ID: 948183) is located between the uhpA and ilvB genes on the chromosome of E. coli K-12. The nucleotide sequence of the ilvN gene and the amino acid sequence of the acetolactate synthase I small subunit encoded by the ilvN gene are shown in SEQ ID NO: 3 and SEQ ID NO: 4, respectively.

The ilvI gene encodes the acetolactate synthase III large subunit (KEGG entry No. b0077). The ilvI gene (GenBank accession No. NC_000913.2; nucleotide positions: 85630 to 87354; Gene ID: 948793) is located between the leoO and ilvH genes on the chromosome of *E. coli* K-12. The nucleotide sequence of the ilvI gene and the amino acid sequence of the acetolactate synthase III large subunit encoded by the ilvI gene are shown in SEQ ID NO: 5 and SEQ ID NO: 6, respectively.

The ilvH gene encodes the acetolactate synthase III small subunit (KEGG entry No. b0078). The ilvH gene (GenBank accession No. NC_000913.2; nucleotide positions: 87357 to 87848; Gene ID: 947267) is located between the ilvI and fruR genes on the chromosome of *E. coli* K-12. The nucleotide sequence of the ilvH gene and the amino acid sequence of the acetolactate synthase III small subunit encoded by the ilvH gene are shown in SEQ ID NO: 7 and SEQ ID NO: 8, respectively.

The ilvY gene encodes DNA-binding transcriptional dual regulator IlvY (LysR family transcriptional regulator, positive regulator for ilvC) (KEGG, Kyoto Encyclopedia of Genes and Genomes, entry No. B3773). The ilvY gene (GenBank accession No. NC_000913.2; nucleotide positions: 3954950 to 3955843, complement; Gene ID: 948284) is located between the ilvA and ilvC genes, both on the opposite strand, on the chromosome of *E. coli* K-12. The nucleotide sequence of the ilvY gene and the amino acid sequence of the IlvY protein encoded by the ilvY gene are shown in SEQ ID NO: 9 and SEQ ID NO: 10, respectively.

The ilvG gene is a pseudogene (KEGG entry No. b4488). The ilvG gene (GenBank accession No. NC_000913.2; nucleotide positions: 3948583 to 3950227; Gene ID: 2847699) is located between the ilvX and ilvM genes on the chromosome of *E. coli* K-12. The nucleotide sequence of the ilvG gene is shown in SEQ ID NO: 31. The ilvG gene may encode the acetolactate synthase II large subunit given it contains substitution of TGA-codon for AAT-codon at position 982 to 984 from the start of the gene, or mutations as described in Lawther R. P. et al., *J. Bacteriol.*, 1982, 159:294-298. The amino acid sequence of acetolactate synthase II large subunit encoded by the ilvG gene in which the TGA-codon is replaced by AAT-codon at position 982 to 984 is shown in SEQ ID NO: 32.

The ilvM gene encodes the acetolactate synthase II small subunit (KEGG entry No. b3769). The ilvM gene (GenBank accession No. NC_000913.2; nucleotide positions: 3950224 to 3950487; Gene ID: 948279) is located between the ilvG and ilvE genes on the chromosome of *E. coli* K-12. The nucleotide sequence of the ilvM gene and the amino acid sequence of the acetolactate synthase II small subunit encoded by the ilvM gene are shown in SEQ ID NO: 33 and SEQ ID NO: 34, respectively.

Since there may be some differences in DNA sequences between the genera or strains of the family Enterobacteriaceae, the acetolactate synthase encoding genes ilvB, ilvN, ilvI, ilvH, ilvG, and ilvM and the transcriptional regulator encoding gene ilvY are not limited to the genes shown in SEQ ID NOs: 1, 3, 5, 7, 31, 33 and 9, but may include genes which are variant nucleotide sequences of or homologous to SEQ ID NOs: 1, 3, 5, 7, 31, 33 and 9, and which encode variants of the IlvB, IlvN, IlvI, IlvH, IlvG, IlvM and IlvY proteins.

The phrase "a variant protein" can mean a protein which has one or several changes in the sequence compared with SEQ ID NOs: 2, 4, 6, 8, 32, 34 and 10, whether they are substitutions, deletions, insertions, and/or additions of amino acid residues, but still maintain an activity similar to that of the IlvB, IlvN, IlvI, IlvH, IlvG, IlvM and IlvY proteins, respectively. The number of changes in the variant protein depends on the position or the type of amino acid residues in the three dimensional structure of the protein. It can be, but is not strictly limited to, 1 to 30, in another example 1 to 15, in another example 1 to 10, and in another example 1 to 5, in SEQ ID NOs: 2, 4, 6, 8, 32, 34 and 10.

The substitution, deletion, insertion, and/or addition of one or several amino acid residues can be a conservative mutation(s) so that the activity and features of the variant protein are maintained, and are similar to those of the IlvB, IlvN, IlvI, IlvH, IlvG, IlvM and IlvY proteins. The representative conservative mutation is a conservative substitution. Examples of conservative substitutions include substitution of Ser or Thr for Ala, substitution of Gln, His or Lys for Arg, substitution of Glu, Gln, Lys, His or Asp for Asn, substitution asn, Glu or Gln for Asp, substitution of Ser or Ala for Cys, substitution asn, Glu, Lys, His, Asp or Arg for Gln, substitution asn, Gln, Lys or Asp for Glu, substitution of Pro for Gly, substitution asn, Lys, Gln, Arg or Tyr for His, substitution of Leu, Met, Val or Phe for Ile, substitution of Ile, Met, Val or Phe for Leu, substitution asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

To evaluate the degree of protein or DNA homology, several calculation methods can be used, such as BLAST search, FASTA search and ClustalW method. The BLAST (Basic Local Alignment Search Tool, www.ncbi.nlm.nih-.gov/BLAST/) search is the heuristic search algorithm employed by the programs blastp, blastn, blastx, megablast, tblastn, and tblastx; these programs ascribe significance to their findings using the statistical methods of Samuel K. and Altschul S. F. ("Methods for assessing the statistical significance of molecular sequence features by using general scoring schemes" *Proc. Natl. Acad. Sci. USA,* 1990, 87:2264-2268; "Applications and statistics for multiple high-scoring segments in molecular sequences". *Proc. Natl. Acad. Sci. USA,* 1993, 90:5873-5877). The computer program BLAST calculates three parameters: score, identity and similarity. The FASTA search method is described by Pearson W. R. ("Rapid and sensitive sequence comparison with FASTP and FASTA", *Methods Enzymol.,* 1990, 183: 63-98). The ClustalW method is described by Thompson J. D. et al. ("CLUSTAL W: improving the sensitivity of progressive multiple sequence alignment through sequence weighting, position-specific gap penalties and weight matrix choice", Nucleic Acids Res., 1994, 22:4673-4680).

Moreover, the ilvB, ilvN, ilvI, ilvH, ilvG, ilvM and ilvY genes can be variant nucleotide sequences. The phrase "a variant nucleotide sequence" can mean a nucleotide sequence which codes "a variant protein". The phrase "a variant nucleotide sequence" can also mean a nucleotide sequence which hybridizes under stringent conditions with the nucleotide sequence complementary to the sequence shown in SEQ ID NOs: 1, 3, 5, 7, 31, 33 and 9, or a probe which can be prepared from the nucleotide sequence under stringent conditions provided that it encodes functional acetolactate synthase or regulatory protein prior to inactivation. "Stringent conditions" include those under which a specific hybrid, for example, a hybrid having homology of not less than 70%, not less than 80%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC, 0.1% SDS, or in another example, 0.1×SSC, 0.1% SDS at 60° C., or in another example at 65° C. Duration of washing depends on the type of membrane used for blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequences shown in SEQ ID NOs: 1, 3, 5, 7, 31, 33 and 9 may also be used. Such a probe can be produced by PCR using oligonucleotides as primers prepared on the basis of the sequences shown in SEQ ID NOs: 1, 3, 5, 7, 31, 33 and 9, and a DNA fragment containing the nucleotide sequence as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after hybridization can be exemplified by 2×SSC, 0.1% SDS at 50° C., or at 60° C., or in another example at 65° C.

As the genes encoding the IlvB, IlvN, IlvI, IlvH, IlvG, IlvM and IlvY proteins of the species *E. coli* have already been elucidated (see above), the variant nucleotide sequences encoding variant proteins of the IlvB, IlvN, IlvI, IlvH, IlvG, IlvM and IlvY proteins can be obtained by PCR (polymerase chain reaction; refer to White T. J. et al., *Trends Genet.*, 1989, 5:185-189) utilizing primers prepared based on the nucleotide sequence of the ilvB, ilvN, ilvI, ilvH, ilvG, ilvM and ilvY genes. Genes encoding the IlvB, IlvN, IlvI, IlvH, IlvG, IlvM and IlvY proteins or their variant proteins of other microorganisms can be obtained in a similar manner.

The phrase "auto-inducible positively regulated promoter" can be a promoter known to those skilled in the art. Conventionally, an auto-inducible positively regulated promoter can mean a promoter which has: a) an increasing activity as the level of a transcription factor or an activator increases, i.e. positive regulation takes place; and b) no or low activity in the absence of a transcription factor or an activator, however it is activated only when bound to a transcription factor or an activator, i.e. inducibility takes place; and c) can be induced by the expression product of the coding gene which is controlled by this promoter, including any post-translationally modified expression products, as well as analogues and derivatives of and complexes with such expression product, in addition, including products such as individual substances or complexes thereof resulted from activity of the expression product of the coding gene, i.e. auto-inducibility takes place.

Auto-inducible positively regulated promoters can be exemplified by the $P_{ilvC}$ promoter (SEQ ID NO: 30) (Wek R. C. and Hatfield G. W., *J. Biol. Chem.*, 1986, 261(5): 2441-2450; Opel M. L. and Hatfield G. W., *Mol. Microbiol*, 2001, 39(1): 191-198) located upstream to the ilvC structural gene, the $P_{cysP}$ promoter located upstream to the cysPUWAM transcription unit, the $P_{cysK}$ promoter located upstream to the cysK structural gene, and the $P_{metR}$ promoter located upstream to the metE structural gene. The $P_{ilvC}$ promoter can be regulated by the IlvY/AL or IlvY/AHB inducer complex. The $P_{cysP}$ and $P_{cysK}$ promoters can be regulated by the O-acetyl-L-serine/CysB auto-inducer complex. The $P_{metR}$ promoter can be regulated by the L-homocystein/MetR auto-inducer complex. The auto-inducible positively regulated promoters are not limited, and may include substitution, deletion, insertion, or addition of one or several nucleotide residues as long as the functionality of the promoter is maintained.

The phrase "auto-inducible negatively regulated promoter" can mean a promoter known in the art. Conventionally, an auto-inducible negatively regulated promoter can mean a promoter which has: a) a decreasing activity as the level of a transcription factor or an activator increases, i.e. negative regulation takes place; and b) no or low activity in the presence of a transcription factor or an activator, however it is becoming activated only when a threshold concentration of a transcription factor or an activator is achieved, i.e. inducibility takes place; and c) can be deregulated by the expression product of the coding gene which is controlled by this promoter, including any post-translationally modified expression products, as well as analogues and derivatives of and complexes with such expression product, in addition, including products resulting from activity of the expression product of the coding gene, i.e. auto-inducibility takes place. The auto-inducible negatively regulated promoters can be exemplified by the $P_{ilvY}$ and $P_{cysB}$ promoters.

The phrase "auto-inducible promoter" can also mean "an auto-regulated promoter", "a self-regulated promoter", "a self-inducible promoter", or the like; regardless it is positively or negatively regulated.

The phrase "auto-inducible positive feedback regulation is mediated by a coinducer" can mean that the expression system accounts for synthesis of a coinducer by regulating expression of a gene encoding the enzyme which is responsible for synthesis of the coinducer. Said coinducer may bind to a regulator protein/DNA complex to activate translation of the gene encoding the enzyme which is responsible for synthesis of the coinducer. Thus, it is apparent that the functionality of the expression system can be mediated by a coinducer.

The phrase "inducible expression system" can mean an expression system in which the transcription level can be modulated by at least about 1.5 fold, or at least 2 fold, or at least 3 fold, or at least 5 fold, or at least 10 fold, or at least 15 fold, or at least 20 fold, or at least 30 fold, or at least 100 fold, or more. An "inducible expression system" can encompass any expression system which can be up-regulated (induced), for example, by a coinducer such as 2-acetolactate, 2-acetohydroxy-2-butanoate, arabinose, lactose, IPTG, etc.), an inducer such as a regulatory protein belonging to the LysR-type proteins family, a stimulus such as heat, cold, etc., or growth conditions such as cell density, acidity (pH), etc. An "inducible expression system" can also encompass any expression system which can be down-regulated (repressed), for example, expression systems which can be down-regulated upon addition of a chemical, a protein, environmental stimulus, and the like.

The phrase "a gene(s) of interest" can mean the gene(s), expression level of which is to be deregulated using the expression system. The exemplary gene(s) of interest may be the gene(s) encoding protein(s) involved in biosynthesis of coinducer, or substrate or precursor of coinducer, or a coinducer synthase. More specifically, the exemplary gene(s) of interest may be large and/or small subunit(s) of AHAS I, II and/or III, or mutant variants thereof. The gene(s) of interest can be exemplified by the ilvBN4 operon genes encoding the mutant AHAS I desensitized to feedback-inhibition by L-valine. The "deregulation of expression level" of a gene(s) of interest can mean attenuation, inactivation or enhancement of expression of said gene(s); the enhancement of expression is one example.

The phrase "operator region" can mean a DNA fragment which is located between a promoter and a structural gene, and influences transcription of a gene under the promoter. The words "promoter" and "promoter region" can also mean a promoter and an operator.

The operator region can be exemplified by the DNA fragment located downstream of the $P_{ilvC}$ or $P_{ilvY}$ promoter and to which the IlvY transcriptional regulator can bind.

The phrase "a regulator of the gene(s) expression system", which can also be referred to as "a regulator of the auto-inducible positively feedback regulated expression system" or "a regulator", can mean a protein belonging to the LysR-type regulatory protein family capable of directly or indirectly regulate transcription of a gene. Exemplary regulatory proteins are shown in Table 1.

The phrase "inactivation of a gene" can mean that the modified gene encodes a completely inactive or non-functional protein. It is also possible that the modified DNA region is unable to naturally express the gene due to deletion of a part of or the entire gene, shifting of the reading frame of the gene, introduction of missense/nonsense mutation(s), or modification of an adjacent region of the gene, including sequences controlling gene expression, such as promoter(s), enhancer(s), attenuator(s), ribosome-binding site(s), etc. Inactivation of the gene can also be performed by conventional methods such as a mutagenesis treatment using ultraviolet irradiation or nitrosoguanidine (N-methyl-N'-nitro-N-nitrosoguanidine), site-directed mutagenesis, gene disruption using homologous recombination, or/and insertion-deletion mutagenesis (Yu D. et al., *Proc. Natl. Acad. Sci. USA*, 2000, 97(12):5978-83; Datsenko K. A. and Wanner B. L., *Proc. Natl. Acad. Sci. USA* 2000, 97(12):6640-45), also called "Red-driven integration" or "λRed-mediated integration".

The phrase "enhancement of a gene expression" or "gene expression is enhanced" can mean that the expression level of the gene is higher than that level in a non-modified strain, for example, a wild-type or parent strain such as *E. coli* MG1655, *E. coli* K12 (VKPM B-7) or *E. coli* B7 ΔilvGM ΔilvIH $P_L$-ilvBN4 strain, due to a genetic modification. Examples of such modification include increasing the copy number of the expressed gene per cell and/or increasing the expression level of the gene by modification of an adjacent region of the gene, including sequences controlling gene expression, such as promoters, enhancers, attenuators, ribosome-binding sites, etc., and other examples. Methods that can be used to enhance expression of the gene can also include introducing the gene into a vector that is able to increase the copy number of the gene in a bacterium of the family Enterobacteriaceae. Examples of the vectors include, but are not limited to, broad-host-range vectors such as pCM110, pRK310, pVK101, pBBR122, pBHR1, and the like. Enhancement of the gene expression can also be achieved by introducing multiple copies of the gene into the chromosomal DNA of a bacterium by, for example, homologous recombination, Mu integration, or the like.

Enhancement of the gene expression can also be achieved by placing the DNA under the control of a potent promoter. For example, the lac promoter, the trp promoter, the trc promoter, the tac promoter, the $P_R$ or the $P_L$ promoters of lambda phage are all known as potent promoters. Potent promoters providing a high level of gene expression in a bacterium belonging to the Enterobacteriaceae family can be used. Alternatively, the effect of a promoter can be enhanced by, for example, introducing a mutation into the promoter region of the gene on the bacterial chromosome to obtain a stronger promoter function, thus resulting in the increased transcription level of the gene located downstream of the promoter. Furthermore, it is known that substitution of several nucleotides in the spacer between ribosome binding site (RBS) and the start codon, especially the sequences immediately upstream to the start codon, profoundly affect the mRNA translatability. For example, a 20-fold range in the expression levels was found, depending on the nature of the three nucleotides preceding the start codon (Gold L. et al., *Annu. Rev. Microbiol.*, 1981, 35:365-403; Hui A. et al., *EMBO J.*, 1984, 3:623-629). The use of a potent promoter can be combined with multiplication of gene copies.

The copy number, presence or absence of the gene and/or operon genes can be measured, for example, by restricting the chromosomal DNA followed by Southern blotting using a probe based on the gene sequence, fluorescence in situ hybridization (FISH), and the like. The level of the gene and/or operon gene's expression can be measured by various known methods including Northern blotting, quantitative RT-PCR, and the like. In addition, the level of gene expression can be determined by measuring the amount of mRNA transcribed from the gene using various well-known methods, including Northern blotting, quantitative RT-PCR, and the like. The amount of the protein coded by the gene can be measured by known methods including SDS-PAGE followed by immunoblotting assay (Western blotting analysis), and the like.

Methods for preparation of plasmid DNA, digestion, ligation and transformation of DNA, selection of an oligonucleotide as a primer, and the like may be ordinary methods well-known to the person skilled in the art. These methods are described, for instance, in Sambrook J., Fritsch E. F. and Maniatis T., "Molecular Cloning: A Laboratory Manual, $2^{nd}$ ed.", Cold Spring Harbor Laboratory Press (1989). Methods for molecular cloning and heterologous gene expression are described in Bernard R. Glick, Jack J. Pasternak and Cheryl L. Patten, "Molecular Biotechnology: principles and applications of recombinant DNA", $4^{th}$ ed., Washington, D.C: ASM Press (2009); Evans Jr., T. C. and Xu M.-Q., "Heterologous gene expression in *E. coli*", 1st ed., Humana Press (2011).

The phrase "activity of an enzyme encoded by the gene is enhanced" can mean that the activity of the enzyme per cell is higher than that in a non-modified strain, for example, a wild-type or a parent strain. For example, the enhanced activity can mean that the number of molecules of the enzyme encoded by the gene per cell or the specific activity per the enzyme molecule is increased, and so forth. The exemplary wild-type *E. coli* K-12 strain containing the wild-type acetolactate synthase may be used for comparison.

The phrase "a biosynthetic pathway", which can also be referred to as "a metabolic pathway" or "a biochemical pathway", can mean a set of anabolic or catabolic (bio)chemical reactions for converting one biomolecule species into another one, more mature biomolecule species towards a desired end-product or useful metabolite. The phrase "a biosynthetic pathway" is usually apparent to one skilled in the art. The desired end-product can be L-amino acid, nucleoside, nucleotide, co-factor, lower or higher alcohol, organic acid, derivatives thereof, protein, and so forth.

The phrase "substrate" can mean any chemical substance, compound or biochemical species that can be converted or is meant to be converted into another substance, compound or biochemical species by the action of an enzyme. The phrase "substrate" may include not only a single compound, but also combinations of compounds such as solutions, mixtures, and other materials which contain at least one substrate, or derivative(s) thereof. The phrase "substrate"

can also mean compounds that provide a carbon source suitable for use as a starting material, for example, any biomass derived sugar, intermediate or end-product metabolites used in a pathway associated with a metabolically engineered microorganism. The chemical substance, compound or biochemical species can be converted into the desired end-product as a consequence of a single reaction catalyzed by an enzyme. Examples of the substrates includes pyruvate and 2-oxobutanoate.

The phrase "precursor" can mean any chemical substance, compound or biochemical species from which another, more mature chemical substance, compound or biochemical species can be formed towards the desired end-product in the biosynthetic pathway. In L-valine biosynthesis the exemplary precursors can be pyruvate, 2-acetolactate, 3-hydroxy-3-methyl-2-oxobutanoate, 2,3-dihydroxy-3-methylbutanoate, and 2-oxoisovalerate. In L-leucine biosynthesis the exemplary precursors can be pyruvate, 2-acetolactate, 3-hydroxy-3-methyl-2-oxobutanoate, 2,3-dihydroxy-3-methylbutanoate, 2-oxoisovalerate, 2-isopropylmalate, and so forth. In L-isoleucine biosynthesis the exemplary precursors can be L-threonine, pyruvate, 2-aceto-2-hydroxybutanoate, 3-hydroxy-3-methyl-2-oxopentanoate, 2,3-dihydroxy-3-methylpentanoate, and so forth.

The phrases "substrate" and "precursor" may be interchangeable.

The phrase "biomolecule" can mean any chemical substance, compound or biochemical species, or product produced by a microorganism. The exemplary biomolecules are proteins, polysaccharides, lipids, nucleic acids, and small molecules such as primary metabolites, secondary metabolites, and natural products.

The phrase "useful metabolite" can mean a chemical substance, compound or biochemical species produced by a microorganism for industrial, feed, food, pharmaceutical or other purposes. The useful metabolite can be exemplified by branched-chain L-amino acids such as L-valine, L-isoleucine, and L-leucine; higher alcohols such as isobutanol, 2-methyl-1-butanol, and 3-methyl-1-butanol; and organic acid such as D-pantothenic acid.

The expression system can be introduced into a bacterium by the methods as described above for enhancement of the gene expression, for example, by using a vector containing the expression system. The expression system can also be introduced into a bacterium by replacing a native promoter of gene(s) of interest with an auto-inducible promoter. The bacterium can contain a gene encoding the LysR-type regulatory protein which positively regulates of the promoter. The expression of the gene encoding the LysR-type regulatory protein can be enhanced, however, the enhancement is not essential. When a promoter is the ilvC promoter and a LysR-type regulatory protein is the ilvY protein, endogenous expression of the ilvY gene is usually sufficient.

3. Method for Producing Useful Metabolites Such as L-Amino Acids, Higher Alcohols, and Organic Acids The method for producing useful metabolites, more specifically L-amino acids, especially branched-chain L-amino acids such as L-valine, L-leucine, and L-isoleucine; higher alcohols such as isobutanol, 2-methyl-1-butanol, and 3-methyl-1-butanol; and organic acids such as D-pantothenic acid, can include the steps of cultivating the bacterium in a culture medium to allow the useful metabolite to be produced, excreted, and accumulated in the culture medium, and collecting the L-amino acid, higher alcohol and/or organic acid from the culture medium.

The cultivation, collection, and the purification of useful metabolites from the medium and the like may be performed in a manner similar to conventional fermentation methods wherein an amino acid, higher alcohol or organic acid is produced using a microorganism. The culture medium for useful metabolite production may be a typical medium that contains a carbon source, a nitrogen source, inorganic ions, and other organic components as required. As the carbon source, saccharides such as glucose, lactose, galactose, fructose, arabinose, maltose, xylose, trehalose, ribose, and hydrolyzates of starches; alcohols such as glycerol, mannitol, and sorbitol; organic acids such as gluconic acid, fumaric acid, citric acid, malic acid, and succinic acid; and the like can be used. As the nitrogen source, inorganic ammonium salts such as ammonium sulfate, ammonium chloride, and ammonium phosphate; organic nitrogen such as of soy bean hydrolyzates; ammonia gas; aqueous ammonia; and the like can be used. Vitamins such as vitamin B1, required substances, for example, organic nutrients such as nucleic acids such as adenine and RNA, or yeast extract, and the like may be present in appropriate, even if trace, amounts. Other than these, small amounts of calcium phosphate, magnesium sulfate, iron ions, manganese ions, and the like may be added, if necessary.

Cultivation can be performed under aerobic conditions for 16 to 72 hours, the culture temperature during cultivation is controlled within 30 to 45° C., or within 30 to 37° C., and the pH is adjusted between 5 and 8, or between 6.5 and 7.2. The pH can be adjusted by using an inorganic or organic acidic or alkaline substance, as well as ammonia gas. Usually, a 1 to 5-day cultivation leads to the accumulation of the target L-amino acid in the liquid medium.

After cultivation, solids such as cells and cell debris can be removed from the liquid medium by centrifugation or membrane filtration, and then the target L-amino acid or organic acid can be recovered from the fermentation liquor by any combination of conventional techniques such as concentration, ion-exchange chromatography and crystallization. The higher alcohols can be recovered from the crude culture medium by, for example, distillation approach followed by the purification using distillation or chromatographic techniques.

EXAMPLES

The present invention will be more precisely explained below with reference to the following non-limiting Examples.

Example 1

Construction of the acetohydroxy acids-regulated expression unit and analysis of its expression using the lacZ reporter gene under various genetic backgrounds Transcription of the ilvYC genes has been well-characterized (Rhee K. et al., *Proc. Natl. Acad. Sci. USA*, 1999, 96(25):14294-14299; Opel M. L. and Hatfield G. W. *Mol. Microbiol.*, 2001, 39(1):191-198). The possibility to use a promoter of the ilvC gene for metabolically-regulated expression system was studied. With this aim, firstly, the cat gene was introduced downstream of the ilvY gene on the chromosome of the *E. coli* MG1655 (ATCC 47076) strain using the λRed-mediated integration. The DNA fragment bearing λattL-cat-λattR cassette was amplified by PCR (polymerase chain reaction) using the oligonucleotide primers P1 (SEQ ID NO: 11) for ilvY-attL region and P2 (SEQ ID NO: 12) for attR-ilvY region, and the plasmid pMW118-λattL-cat-λattR (Katashkina Zh. I. et al., Mol. Biol. (Mosk.), 2005, 39(5):823-831) as the template. The DNA fragment obtained was introduced into the E. coli MG1655/pKD46 strain by electrotransformation using "Bio-Rad" electroporator (USA) (No. 165-2098, version 2-89) according to the manufacturer's instructions. As a result, the chloramphenicol resistant transformant E. coli MG1655cat-ilvY harboring the chloramphenicol resistance marker (λattL-cat-λattR, Cm®) on the chromosome upstream the ilvY gene was obtained. The recombinant plasmid pKD46 (Datsenko K. A. and Wanner B. L., Proc. Natl. Acad. Sci. USA, 2000, 97:6640-6645) with the temperature-sensitive replicon was used as the donor of the phage λ-derived genes responsible for the λRed-mediated recombination system. The E. coli MG1655 strain containing the recombinant plasmid pKD46 can be obtained from the E. coli Genetic Stock Center, Yale University, New Haven, USA, the accession number is CGSC7669. After integration of the plasmid pKD46 into the E. coli MG1655 strain, the E. coli MG1655/pKD46 strain was obtained.

Secondly, the fragment cat-ilvY-$P_{ilvC}$ including λattL-cat-λattR, ilvY gene, and intergenic region ilvY-ilvC with $P_{ilvC}$ promoter was PCR-amplified using the oligonucleotide primers P3 (SEQ ID NO: 13) for attL-lacZ region and P4 (SEQ ID NO: 14) for ilvCp-lacZ region, and the chromosome of the E. coli MG1655cat-ilvY strain as the template. The PCR-fragment obtained was inserted into the E. coli MG1655/pKD46 chromosome region upstream the lacZ gene by means of λRed-mediated integration. As a result, the strain E. coli MG1655cat-ilvY-$P_{ilvC}$-lacZ was obtained. Cm®-resistant colonies were selected on the plates containing the lysogenic broth (Sambrook, J. and Russell, D. W. (2001) Molecular Cloning: A Laboratory Manual (3$^{rd}$ ed.). Cold Spring Harbor Laboratory Press), agar 1.5%, and chloramphenicol 40 mg/l. The insertion was verified by PCR. For this purpose, colonies which grew within 24 h were tested for the presence of cat-ilvY-$P_{ilvC}$-lacZ fragment instead of the native lacZ gene by PCR using primers P13 (SEQ ID NO: 23) and P14 (SEQ ID NO: 24). For this purpose, a freshly isolated colony was suspended in 20 μl water, and then 1 μl of obtained suspension was used for PCR. The temperature profile was the following: initial DNA denaturation for 5 min at 94° C. followed by 30 cycles of: denaturation at 94° C. for 30 sec, annealing at 53° C. for 30 sec, and elongation at 72° C. for 3 min; and the final elongation for 7 min at 72° C. A few Cm® colonies tested should contain the desired 3053 bp DNA fragment, confirming presence of the cat-ilvY-$P_{ilvC}$-lacZ DNA fragment instead of the 288 bp native lacZ gene. One of the obtained strains was cured from the thermosensitive plasmid pKD46 by culturing at 37° C., and the resulting strain was named as E. coli MG1655 cat-ilvY-$P_{ilvC}$-lacZ.

In order to provide data for the expression level of AHAS I-encoding genes (ilvBN and ilvBN4), the expression level of the reporter lacZ gene under control of the $P_{ilvC}$ promoter was estimated under various genetic backgrounds (Table 2). Strains, additionally containing deletion of the ilvAYC genes, were also analyzed. The ΔilvAYC-Km® modification was introduced by means of P1-transductions (Miller J. H. (1972) Experiments in molecular genetics. Cold Spring Harbor Laboratory, Cold Spring Harbor).

All modifications were combined by means of P1-transductions and strains obtained were cured from "excisable" markers as described in EP1942183.

The ilvAYC deletion was constructed in two steps using the λRed-mediated integration. Firstly, the PCR-fragment was obtained using the oligonucleotide primers P5 (SEQ ID NO: 15) and P6 (SEQ ID NO: 16), and the plasmid pMW118-λattL-kan-λattR (Katashkina Zh. I. (2002) Development of the methods for targeted modification of E. coli genetic loci for the construction of amino-acids-producing strains. PhD Thesis. Moscow) as the template harboring the kanamycin resistance marker (λattL-kan-λattR, Km®). Secondly, the fragment obtained was introduced into the E. coli MG1655/pKD46 strain by electrotransformation as described above. Kanamycin resistant clones with deleted ilvAYC genes were selected on kanamycin-containing plates as described above. As a result, the E. coli MG1655ΔilvAYC::Km® strain was obtained. The insertion was verified by PCR. With this aim, colonies which grew within 24 h were tested for the presence of ΔilvAYC::Km® fragment instead of the native ilvAYC genes by PCR using primers P15 (SEQ ID NO: 25) and P16 (SEQ ID NO: 26). For this purpose, a freshly isolated colony was suspended in 20 μl water, and then 1 μl of obtained suspension was used for PCR. The temperature profile was the following: initial DNA denaturation for 5 min at 94° C. followed by 30 cycles of: denaturation at 94° C. for 30 sec, annealing at 57° C. for 30 sec, and elongation at 72° C. for 2 min; and the final elongation for 7 min at 72° C. A few Km® colonies tested should contain the desired 1761 bp DNA fragment, confirming presence of the ΔilvAYC::Km® DNA fragment instead of the 2926 bp native ilvAYC genes. One of the obtained strains was cured from the thermosensitive plasmid pKD46 by culturing at 37° C., and the resulting strain was named as E. coli MG1655 ΔilvAYC::Km®.

The modifications cat-ilvY-$P_{ilvC}$-lacZ, ΔilvAYC::Km®, ΔilvGM, ΔilvIH, ΔilvBN, $P_L$-ilvBN and $P_L$-ilvBN4 were introduced into E. coli K12 (VKPM B-7) strain using P1-transduction. Construction of ΔilvBN, ΔilvGM, ΔilvIH, and $P_L$-ilvBN is described in EP1942183. The strain VKPM B-7 (referred to as B7) can be replaced by other substrains of K12 such as K12 MG1655 which is available from American Type Culture Collection (P.O. Box 1549, Manassas, Va. 20108, United States of America) (ATCC47076).

As a result, the strains listed in Table 2 were obtained.

TABLE 2

Effect of the various genetic backgrounds on $P_{ilvC}$-dependent transcription. Activity of β-galactosidase LacZ.

| Strain | Specific activity of β-galactosidase, Miller's units |
|---|---|
| B7 (+IPTG, 1 mM) | 1200 |
| B7 ΔilvBN ΔilvGM ΔilvIH cat-ilvY-$P_{ilvC}$-lacZ | 10 |
| B7 ΔilvGM ΔilvIH $P_L$-ilvBN cat-ilvY-$P_{ilvC}$-lacZ | 940 |
| B7 ΔilvGM ΔilvIH $P_L$-ilvBN4 cat-ilvY-$P_{ilvC}$-lacZ | 3700 |
| B7 ΔilvGM ΔilvIH $P_L$-ilvBN ΔilvAYC-Km$^R$ cat-ilvY-$P_{ilvC}$-lacZ | 4400 |
| B7 ΔilvGM ΔilvIH$P_L$-ilvBN4 ΔilvAYC-Km$^R$ cat-ilvY-$P_{ilvC}$-lacZ | 4400 |

For the measurement of β-galactosidase activity, the strains were grown to the middle-logarithmic phase in M9:LB (9:1, v/v) medium supplemented with glucose (0.4%, w/v). The medium for the strains having ilvAYC deletion and AHAS-deficient strains was additionally supplemented with Ile (25 mg/l) and Val (25 mg/l). Activity of β-galactosidase was measured according to Miller's method (Miller J. H. (1972) Experiments in molecular genetics. Cold Spring Harbor Laboratory, Cold Spring Harbor). The data presented in Table 2 indicate that expression level of the reporter lacZ gene under $P_{ilvC}$ promoter varies within the range of more than two orders of magnitude depending on the genetic background. The maximal expression level was provided by the *E. coli* strains modified to overexpress L-valine resistant AHAS I (the product of the ilvBN4 genes) or/and containing inactivated the isomeroreductase IlvC encoding gene (ilvC).

Example 2

Construction of the Mutant *E. coli* B7 ΔilvGM ΔilvIH Cat-ilvY-P$_{ilvC}$-ilvBN4 Strain The *E. coli* B7 ΔilvGM ΔilvIH P$_L$-ilvBN4 strain was modified to contain the cat-ilvY-P$_{ilvC}$ expression unit obtained as described in Example 1. The phage promoter P$_L$ upstream of the ilvBN4 genes was substituted for cat-ilvY-P$_{ilvC}$ regulatory region using λRed-mediated integration in the *E. coli* B7 ΔilvIH ΔilvGM P$_L$-ilvBN4 strain (construction of this strain is described in EP1942183). For this purpose, the DNA-fragment containing cat-ilvY-P$_{ilvC}$ expression cassette flanked with the short regions adjacent to the ilvB gene was PCR-amplified using the oligonucleotide primers P7 (SEQ ID NO: 17) and P8 (SEQ ID NO: 18), and the chromosome of *E. coli* MG1655 cat-ilvY-P$_{ilvC}$-lacZ strain as the template. The PCR-fragment obtained was introduced by electrotransformation into the *E. coli* B7 ΔilvIH ΔilvGM P$_L$-ilvBN4/pKD46 strain as described above. As a result, the strain *E. coli* B7 ΔilvIH ΔilvGM cat-ilvY-P$_{ilvC}$-ilvBN4 was obtained, in which the λ-phage promoter P$_L$ upstream the feedback-resistant AHAS I-encoding operon genes ilvBN4 was replaced with the auto-inducible promoter P$_{ilvC}$. The replacement was verified by PCR. With this aim, colonies which grew within 24 h were tested for the presence of cat-ilvY-P$_{ilvC}$-ilvBN4 fragment, introduced instead of the P$_L$-ilvBN4 cassette, by PCR using primers P17 (SEQ ID NO: 27) and P18 (SEQ ID NO: 28). For this purpose, a freshly isolated colony was suspended in 20 μl water, and then 1 μl of obtained suspension was used for PCR. The temperature profile was the following: initial DNA denaturation for 5 min at 94° C. followed by 30 cycles of: denaturation at 94° C. for 30 sec, annealing at 59° C. for 30 sec, and elongation at 72° C. for 2 min; and the final elongation for 7 min at 72° C. A few Cm® colonies tested should contain the desired 2865 bp DNA fragment, confirming presence of the cat-ilvY-P$_{ilvC}$-ilvBN4 DNA fragment instead of the 382 bp initial P$_L$-ilvBN4 construct. One of the obtained strains was cured from the thermosensitive plasmid pKD46 by culturing at 37° C., and the resulting strain was named as *E. coli* B7 ΔilvGM ΔilvIH cat-ilvY-P$_{ilvC}$-ilvBN4.

Example 3

Properties of the mutant *E. coli* B7 ΔilvGM ΔilvIH cat-ilvY-P$_{ilvC}$-ilvBN4 Strain Cells were grown to the middle-logarithmic phase in M9:LB (9:1, v/v) medium supplemented with glucose (0.4%, w/v). Activity of AHAS I in crude cells extracts was measured with or without addition of 10 mM L-Val according to the assay described in Stormer F. and Umbarger H., *Biochem. Biophys. Res. Commun.*, 1964, 17(5):587-592. The means of triplicate experiments are presented in Table 3. The data show that the cat-ilvY-P$_{ilvC}$ regulatory region provides the increased level of AHAS I expression.

TABLE 3

Activity of AHAS I measured in strains with cat-ilvY-P$_{ilvC}$-ilvBN4 expression unit.

| | AHAS I activity, nmol/min*mg | |
|---|---|---|
| Strain | without L-Val | with L-Val, 10 mM (percent of value, measured without L-Val addition) |
| B7 ΔilvGM ΔilvIH P$_L$-ilvBN4 (control) | 59 | 51 (86%) |
| B7 ΔilvGM ΔilvIH cat-ilvY-P$_{ilvC}$-ilvBN4 cl.1 | 91 | 80 (88%) |
| B7 ΔilvGM ΔilvIH cat-ilvY-P$_{ilvC}$-ilvBN4 cl.4 | 121 | 106 (88%) |

Example 4

Production of L-Valine by the *E. coli* B7 ΔilvGM ΔilvIH Cat-ilvY-P$_{ilvC}$-ilvBN4 Strain The modified *E. coli* B7 ΔilvGM ΔilvIH cat-ilvY-P$_{ilvC}$-ilvBN4 and the control B7 ΔilvGM ΔilvIH P$_L$-ilvBN4 strains were each cultivated at 32° C. for 18 hours in Luria-Bertani broth (also referred to as lysogenic broth as described in Sambrook, J. and Russell, D. W. (2001) Molecular Cloning: A Laboratory Manual (3$^{rd}$ ed.). Cold Spring Harbor Laboratory Press). Then, 0.2 mL of the obtained culture was inoculated into 2 mL of a fermentation medium in 20×200 mm test-tubes and cultivated at 30° C. for 60 hours on a rotary shaker at 250 rpm.

The composition of the fermentation medium (g/L):

| | |
|---|---|
| Glucose | 60.0 |
| (NH$_4$)$_2$SO$_4$ | 15.0 |
| KH$_2$PO$_4$ | 1.5 |
| MgSO$_4$ × 7H$_2$O | 1.0 |
| Thiamine-HCl | 0.1 |
| CaCO$_3$ | 25, |
| with the addition of LB medium: 10% (v/v) | |

The fermentation medium was sterilized at 116° C. for 30 min, except that glucose and CaCO$_3$ were sterilized separately and as follows: glucose at 110° C. for 30 min, CaCO$_3$ at 116° C. for 30 min. The pH was adjusted to 7.0 by KOH solution.

After cultivation, accumulated L-valine was measured using thin-layer chromatography (TLC). TLC plates (10×20 cm) were coated with 0.11 mm layers of Sorbfil silica gel containing non-fluorescent indicator (Sorbpolymer, Krasnodar, Russian Federation). Samples were applied to the plates with the Camag Linomat 5 sample applicator. The Sorbfil plates were developed with a mobile phase consisting of iso-propanol:ethylacetate: 25% aqueous ammonia: water (16:16:5:10, v/v). A solution of ninhydrin (2%, w/v) in acetone was used as the visualizing reagent. After development, plates were dried and scanned with the Camag TLC Scanner 3 in absorbance mode with detection at 520 nm using winCATS software (version 1.4.2).

The results of 4 independent test-tube fermentations are shown in Table 4. As it can be seen from the Table 4, the modified *E. coli* B7 ΔilvGM ΔilvIH cat-ilvY-P$_{ilvC}$-ilvBN4 strain caused a higher amount of accumulation of L-valine as compared with the parent *E. coli* B7 ΔilvGM ΔilvIH P$_L$-ilvBN4 strain.

TABLE 4

Production of L-valine by the modified E. coli strain. The values are mean ± SD, where SD represents standard deviation.

| Strain | OD$_{540\,nm}$ | L-Val, g/L |
|---|---|---|
| B7 ΔilvGM ΔilvIH P$_L$-ilvBN4 (control) | 59 | 4.2 ± 0.4 |
| B7 ΔilvGM ΔilvIH cat-ilvY-P$_{ilvC}$-ilvBN4 | 53 | 5.7 ± 0.5 |

Example 5

Construction of the E. coli B7 ΔilvGM ΔilvIH ilvY$^{inactive}$-P$^{ilvC}$-ilvBN4 Strain The expression cassette ilvY-P$_{ilvC}$-ilvBN4 contains the ilvY gene encoding the positive LysR-type regulator of P$_{ilvC}$-mediated expression. Therefore, a strain harboring this cassette possesses two copies of ilvY gene: one copy is located in its native locus on the chromosome and another copy is located upstream the ilvBN4 operon. To elucidate, whether the positive effect from the ilvY-P$_{ilvC}$-ilvBN4 cassette is concerned with the duplication of ilvY gene, the ilvY gene was inactivated in the ilvY-P$_{ilvC}$-ilvBN4 expression cassette. The nucleotide sequence of the ilvY gene was modified in such a way that, apart from the inactivation of the ilvY gene, the regulatory region of the ilvBN4 operon genes remained unaltered. More specifically, a DNA-fragment of the length of 31 nucleotides was inserted into the ilvY gene of the ilvY-P$_{ilvC}$-ilvBN4 expression cassette to replace the fifth codon (GAT) of the structural part of the ilvY gene by the "stop"-codon TGA.

The inactivation of the IlvY gene was performed as follows. Firstly, the PCR-fragment harboring the λattL-cat-λattR cassette with the regions adjacent to ilvY internal part was obtained using the oligonucleotide primers P9 (SEQ ID NO: 19) and P10 (SEQ ID NO: 20), and the plasmid pMIV5-JS as the template. The plasmid pMIV5-JS was constructed as described in EP1942183. The E. coli MG1655/pKD46 cells were electrotransformed with the PCR-fragment obtained and the chloramphenicol resistant transformants were selected as described above. As a result, the E. coli MG1655 ilvY::cat strain containing insertion of the chloramphenicol resistant marker (Cm®) in the ilvY coding region was obtained. The insertion was verified by PCR as follows. The colonies which grew within 24 h were tested for the presence of ilvY::cat DNA fragment instead of the native ilvY gene by PCR using primers P11 (SEQ ID NO: 21) and P12 (SEQ ID NO: 22). For this purpose, a freshly isolated colony was suspended in 20 μl water, and then 1 μl of obtained suspension was used for PCR. The temperature profile was the following: initial DNA denaturation for 5 min at 94° C. followed by 30 cycles of: denaturation at 94° C. for 30 sec, annealing at 55° C. for 30 sec, and elongation at 72° C. for 1 min 30 sec; and the final elongation for 7 min at 72° C. A few Cm® colonies tested should contain the desired 1603 bp DNA fragment, confirming presence of the ilvY::cat DNA fragment instead of the 297 bp native ilvY region. One of the obtained strains was cured from the thermosensitive plasmid pKD46 by culturing at 37° C., and the resulting strain was named as E. coli MG1655 ilvY::cat.

The E. coli B7 ΔilvGM ΔilvIH cat-ilvY-P$_{ilvC}$-ilvBN4 strain (see Example 2) was cured from the Cm®-marker (cat) by transient introduction of pMWts-λInt/Xis plasmid (Katashkina Zh. I. et al., Mol. Biol. (Mosk.), 2005, 39(5): 823-831) resulted in the marker-less E. coli B7 ΔilvGM ΔilvIH ilvY-P$_{ilvC}$-ilvBN4 strain. The ilvAYC genes were deleted from the E. coli B7 ΔilvGM ΔilvIH ilvY-P$_{ilvC}$-ilvBN4 strain by P1-transduction as described above using E. coli MG1655 ΔilvAYC::Km® (see Example 1) as a donor. Having cloned the λRed-genes on the plasmid pKD46, the E. coli B7 ΔilvGM ΔilvIH ilvY-P$_{ilvC}$-ilvBN4 ΔilvAYC::Km® strain was electrotransformed by the PCR-fragment harboring the λattL-cat-λattR cassette with the regions adjacent to ilvY internal part. This PCR-fragment was amplified with the oligonucleotide primers P11 (SEQ ID NO: 21) and P12 (SEQ ID NO: 22), and the chromosome of the E. coli MG1655 ilvY::cat strain as the template. As a result, the E. coli B7 ΔilvGM ΔilvIH ΔilvAYC::Km® ilvY::cat-P$_{ilvC}$-ilvBN4 strain was obtained, which was used further as a donor strain to transduce the ilvY::cat-P$_{ilvC}$-ilvBN4 cassette into the E. coli B7 ΔilvGM ΔilvIH ilvY-P$_{ilvC}$-ilvBN4 strain. The P1-transduction was performed as described above. Verification of the cassette ilvY::cat-P$_{ilvC}$-ilvBN4 was performed by PCR. With this aim, colonies which grew within 24 h were tested for the presence of ilvY::cat-P$_{ilvC}$-ilvBN4 DNA fragment instead of the cassette ilvY-P$_{ilvC}$-ilvBN4 by PCR using primers P11 (SEQ ID NO: 21) and P19 (SEQ ID NO: 29). For this purpose, a freshly isolated colony was suspended in 20 μl water, and then 1 μl of obtained suspension was used for PCR. The temperature profile was the following: initial DNA denaturation for 5 min at 94° C. followed by 30 cycles of: denaturation at 94° C. for 30 sec, annealing at 58° C. for 30 sec, and elongation at 72° C. for 2 min; and the final elongation for 7 min at 72° C. A few Cm® colonies tested should contain the desired 1654 bp DNA fragment, confirming presence of the ilvY::cat-P$_{ilvC}$-ilvBN4 DNA fragment instead of the 339 bp initial ilvY-P$_{ilvC}$-ilvBN4 construct. One of the obtained strains was cured from the thermosensitive plasmid pKD46 by culturing at 37° C., and the resulting strain was named as E. coli B7 ΔilvGM ΔilvIH ΔilvAYC::Km® This strain was used further as a donor strain to transduce the ilvY::cat-P$_{ilvC}$-ilvBN4 cassette into the E. coli B7 ΔilvGM ΔilvIH ilvY-P$_{ilvC}$-ilvBN4 strain as described above. As a result, the strain E. coli B7 ΔilvGM ΔilvIH ilvY::cat-P$_{ilvC}$-ilvBN4 was obtained which possesses only one active copy of the ilvY gene located in its native locus due to inactivation of the ilvY gene copy in the ilvY::cat-P$_{ilvC}$-ilvBN4 cassette as described above. The cat gene was eliminated using the transient introduction of pMWts-λInt/Xis plasmid. As a result, the marker-less strain E. coli B7 ΔilvGM ΔilvIH ilvY$^{inactive}$-P$_{ilvC}$-ilvBN4 was obtained.

Example 6

Production of L-Valine by the E. coli B7 ΔilvGM ΔilvIH ilvY$^{inactive}$-P$_{ilvC}$-ilvBN4 Strain The modified E. coli B7 ΔilvGM ΔilvIH ilvY$^{inactive}$-P$_{ilvC}$-ilvBN4 and the control B7 ΔilvGM ΔilvIH P$_L$-ilvBN4 and B7 ΔilvGM ΔilvIH cat-ilvY-P$_{ilvC}$-ilvBN4 strains were each cultivated at 32° C. for 18 hours in Luria-Bertani broth (also referred to as lysogenic broth as described in Sambrook, J. and Russell, D. W. (2001) Molecular Cloning: A Laboratory Manual (3$^{rd}$ ed.). Cold Spring Harbor Laboratory Press). Then, 0.2 mL of the obtained culture was inoculated into 2 mL of a fermentation medium in 20×200 mm test-tubes and cultivated at 30° C. for 60 hours on a rotary shaker at 250 rpm.

The composition of the fermentation medium (g/L):

| | |
|---|---|
| Glucose | 60.0 |
| (NH$_4$)$_2$SO$_4$ | 15.0 |
| KH$_2$PO$_4$ | 1.5 |
| MgSO$_4$ × 7H$_2$O | 1.0 |
| Thiamine-HCl | 0.1 |
| CaCO$_3$ | 25, |
| with the addition of LB medium: 10% (v/v) | |

The fermentation medium was sterilized at 116° C. for 30 min, except that glucose and CaCO$_3$ were sterilized separately and as follows: glucose at 110° C. for 30 min, CaCO$_3$ at 116° C. for 30 min. The pH was adjusted to 7.0 by KOH solution.

After cultivation, accumulated L-valine was measured using thin-layer chromatography (TLC). TLC plates (10×20 cm) were coated with 0.11 mm layers of Sorbfil silica gel containing non-fluorescent indicator (Sorbpolymer, Krasnodar, Russian Federation). Samples were applied to the plates with the Camag Linomat 5 sample applicator. The Sorbfil plates were developed with a mobile phase consisting of iso-propanol:ethylacetate: 25% aqueous ammonia: water (16:16:5:10, v/v). A solution of ninhydrin (2%, w/v) in acetone was used as the visualizing reagent. After development, plates were dried and scanned with the Camag TLC Scanner 3 in absorbance mode with detection at 520 nm using winCATS software (version 1.4.2).

The results of 4 independent test-tube fermentations are shown in Table 5. As it can be seen from the Table 5, the modified E. coli B7 ΔilvGM ΔilvIH ilvY$^{inactive}$-P$_{ilvC}$-ilvBN4 strain caused a higher amount of accumulation of L-valine as compared with the parent E. coli B7 ΔilvGM ΔilvIH P$_L$-ilvBN4 strain. Moreover, the inactivation of the ilvY gene in the E. coli B7 ΔilvGM ΔilvIH cat-ilvY-P$_{ilvC}$-ilvBN4 strain does not have negative influence on L-valine production by the strain.

Table 5.
Production of L-valine by the modified E. coli strain. The values are mean±SD, where SD represents standard deviation.

| Strain | OD$_{540\,nm}$ | L-Val, g/L |
|---|---|---|
| B7 ΔilvGM ΔilvIH P$_L$-ilvBN4 (control) | 59 | 3.7 ± 0.4 |
| B7 ΔilvGM ΔilvIH cat-ilvY-P$_{ilvC}$-ilvBN4 (control) | 52 | 5.5 ± 0.2 |
| B7 ΔilvGM ΔilvIH ilvY$^{inactive}$-P$_{ilvC}$-ilvBN4 | 56 | 5.7 ± 0.5 |

While the invention has been described in detail with reference to preferred embodiments thereof, it will be apparent to one skilled in the art that various changes can be made, and equivalents employed, without departing from the scope of the invention. All the cited references herein are incorporated as a part of this Application by reference.

EXPLANATION OF SEQUENCE LISTING

SEQ ID NO: 1: nucleotides sequence of ilvB
SEQ ID NO: 2: amino acid sequence of a wild-type acetolactate synthase I large subunit
SEQ ID NO: 3: nucleotides sequence of ilvN
SEQ ID NO: 4: amino acid sequence of a wild-type acetolactate synthase I small subunit
SEQ ID NO: 5: nucleotides sequence of ilvI
SEQ ID NO: 6: amino acid sequence of a wild-type acetolactate synthase III large subunit
SEQ ID NO: 7: nucleotides sequence of ilvH
SEQ ID NO: 8: amino acid sequence of a wild-type acetolactate synthase III small subunit
SEQ ID NO: 9: nucleotides sequence of ilvY
SEQ ID NO: 10: amino acid sequence of IlvY
SEQ ID NOS: 11-29: nucleotides sequence of primers
SEQ ID NO: 30: nucleotides sequence of P$_{ilvC}$ promoter
SEQ ID NO: 31: nucleotides sequence of ilvG
SEQ ID NO: 32: amino acid sequence of acetolactate synthase II large subunit
SEQ ID NO: 33: nucleotides sequence of ilvM
SEQ ID NO: 34: amino acid sequence of acetolactate synthase II small subunit

The invention claimed is:

1. A gene expression system comprising:
   A) LysR-type protein-regulated transcriptional machinery comprising a promoter and an operator, the expression of the transcriptional machinery is positively regulated by the LysR-type regulatory protein and a coinducer, and
   B) a gene(s) of interest to which said transcriptional machinery is operably linked, wherein the gene(s) of interest encode(s) a protein(s) involved in biosynthesis of said coinducer, a substrate, or a precursor of said coinducer, whereby auto-inducible positive feedback regulation of said expression system is mediated by said coinducer, wherein said promoter is $P_{ilvC}$ promoter, said LysR-type regulatory protein is IlvY protein, and said coinducer is 2-acetolactatic acid or a salt thereof, or 2-aceto-2-hydroxybutyric acid or a salt thereof, and wherein said gene(s) of interest encode(s) acetohydroxy-acid synthetase.

2. The expression system according to claim 1, wherein said system is from a bacterium belonging to the family Enterobacteriaceae or Pseudomonadaceae.

3. The expression system according to claim 1, wherein said system is from a bacterium belonging to the family Enterobacteriaceae.

4. The expression system according to claim 3, wherein said system is from a bacterium belonging to the genus *Escherichia*.

5. The expression system according to claim 4, wherein said bacterium belongs to the species *Escherichia coli*.

6. The expression system according to claim 1, wherein said system is from the biosynthetic pathway of an L-amino acid selected from the group consisting of a branched-chain L-amino acid, L-lysine, L-cystein, L-methionine, and L-tryptophan.

7. The expression system according to claim 6, wherein said system is from the branched-chain L-amino acid biosynthetic pathway.

8. The expression system according to claim 1, wherein the coinducer is 2-acetolactic acid or a salt thereof.

9. The expression system according to claim 1, wherein said genes of interest encode proteins selected from the group consisting of:
(A) a combination of A1 and A2:
  (A1) a protein comprising the amino acid sequence of SEQ ID NO: 2; or a protein comprising the amino acid sequence of SEQ ID NO: 2, but which includes substitution, deletion, insertion, or addition of one or several amino acid residues and has acetolactate synthase activity when in the presence of a protein of A2;
  (A2) a protein comprising the amino acid sequence of SEQ ID NO: 4; or a protein comprising the amino acid sequence of SEQ ID NO: 4, but which includes substitution, deletion, insertion, or addition of one or several amino acid residues and has acetolactate synthase activity when in the presence of a protein of A1;
(B) a combination of B1 and B2:
  (B1) a protein comprising the amino acid sequence of SEQ ID NO: 6; or a protein comprising the amino acid sequence of SEQ ID NO: 6, but which includes substitution, deletion, insertion, or addition of one or several amino acid residues and has acetolactate synthase activity when in the presence of a protein of B2;
  (B2) a protein comprising the amino acid sequence of SEQ ID NO: 8; or a protein comprising the amino acid sequence of SEQ ID NO: 8, but which includes substitution, deletion, insertion, or addition of one or several amino acid residues and has acetolactate synthase activity when in the presence of a protein of B1; and
(C) a combination of C1 and C2:
  (C1) a protein comprising the amino acid sequence of SEQ ID NO: 32; or a protein comprising the amino acid sequence of SEQ ID NO: 32, but which includes substitution, deletion, insertion, or addition of one or several amino acid residues and has acetolactate synthase activity when in the presence of a protein of C2;
  (C2) a protein comprising the amino acid sequence of SEQ ID NO: 34; or a protein comprising the amino acid sequence of SEQ ID NO: 34, but which includes substitution, deletion, insertion, or addition of one or several amino acid residues and has acetolactate synthase activity when in the presence of a protein of C1.

10. The expression system according to claim 9, wherein said acetohydroxy-acid synthetase is a mutant acetolactate synthase I resistant to feedback inhibition by L-valine.

11. The expression system according to claim 1, wherein said operator comprises a region to which said LysR-type regulatory protein binds.

12. The expression system according to claim 1, wherein said LysR-type regulatory protein is selected from the group consisting of:
(D) a protein comprising the amino acid sequence of SEQ ID NO: 10; and
(E) a protein comprising the amino acid sequence of SEQ ID NO: 10, but which includes substitution, deletion, insertion, or addition of one or several amino acid residues and has LysR-type regulatory protein activity.

13. The expression system according to claim 1, wherein said promoter comprises:
(F) a DNA comprising the nucleotide sequence of SEQ ID NO: 30; or
(G) a DNA comprising the nucleotide sequence of SEQ ID NO: 30, but which includes substitution, deletion, insertion, or addition of one or several nucleotide residues and has activity of the nucleotide sequence of SEQ ID NO: 30.

14. An L-amino acid-producing bacterium belonging to the family Enterobacteriaceae, wherein said bacterium has been modified to contain the expression system according to claim 1.

15. The bacterium according to claim 14, wherein said bacterium contains a gene encoding the LysR-type regulatory protein.

16. The bacterium according to claim 14, wherein said bacterium belongs to the genus *Escherichia*.

17. The bacterium according to claim 16, wherein said bacterium belongs to the species *Escherichia coli*.

18. The bacterium according to claim 14, wherein said L-amino acid is branched-chain L-amino acid.

19. The bacterium according to claim 18, wherein said branched-chain L-amino acid is selected from the group consisting of L-valine, L-leucine, and L-isoleucine.

20. A method for producing a branched-chain L-amino acid comprising:
(i) cultivating the bacterium according to claim 18 in a culture medium so that said branched-chain L-amino acid is accumulated in the culture medium; and
(ii) collecting said branched-chain L-amino acid from the culture medium.

21. The method for producing the branched-chain L-amino acid according to claim 20, wherein said branched-chain L-amino acid is selected from the group consisting of L-valine, L-leucine, and L-isoleucine.

* * * * *

SEQUENCE LISTING

```
<160> NUMBER OF SEQ ID NOS: 34

<210> SEQ ID NO 1
<211> LENGTH: 1689
<212> TYPE: DNA
<213> ORGANISM: Escherichia coli
<220> FEATURE:
<221> NAME/KEY: CDS
<222> LOCATION: (1)..(1689)

<400> SEQUENCE: 1 atg gca agt tcg ggc aca aca tcg acg cgt aag cgc ttt acc ggc gca      48
Met Ala Ser Ser Gly Thr Thr Ser Thr Arg Lys Arg Phe Thr Gly Ala
1               5                   10                  15 gaa ttt atc gtt cat ttc ctg gaa cag cag ggc att aag att gtg aca      96
Glu Phe Ile Val His Phe Leu Glu Gln Gln Gly Ile Lys Ile Val Thr
            20                  25                  30 ggc att ccg ggc ggt tct atc ctg cct gtt tac gat gcc tta agc caa     144
Gly Ile Pro Gly Gly Ser Ile Leu Pro Val Tyr Asp Ala Leu Ser Gln
        35                  40                  45 agc acg caa atc cgc cat att ctg gcc cgt cat gaa cag ggc gcg ggc     192
Ser Thr Gln Ile Arg His Ile Leu Ala Arg His Glu Gln Gly Ala Gly
```

```
            50                  55                  60
ttt atc gct cag gga atg gcg cgc acc gac ggt aaa ccg gcg gtc tgt       240
Phe Ile Ala Gln Gly Met Ala Arg Thr Asp Gly Lys Pro Ala Val Cys
 65                  70                  75                  80 atg gcc tgt agc gga ccg ggt gcg act aac ctg gtg acc gcc att gcc       288
Met Ala Cys Ser Gly Pro Gly Ala Thr Asn Leu Val Thr Ala Ile Ala
                 85                  90                  95 gat gcg cgg ctg gac tcc atc ccg ctg att tgc atc act ggt cag gtt       336
Asp Ala Arg Leu Asp Ser Ile Pro Leu Ile Cys Ile Thr Gly Gln Val
            100                 105                 110 ccc gcc tcg atg atc ggc acc gac gcc ttc cag gaa gtg gac acc tac       384
Pro Ala Ser Met Ile Gly Thr Asp Ala Phe Gln Glu Val Asp Thr Tyr
        115                 120                 125 ggc atc tct atc ccc atc acc aaa cac aac tat ctg gtc aga cat atc       432
Gly Ile Ser Ile Pro Ile Thr Lys His Asn Tyr Leu Val Arg His Ile
    130                 135                 140 gaa gaa ctc ccg cag gtc atg agc gat gcc ttc cgc att gcg caa tca       480
Glu Glu Leu Pro Gln Val Met Ser Asp Ala Phe Arg Ile Ala Gln Ser
145                 150                 155                 160 ggc cgc cca ggc ccg gtg tgg ata gac att cct aag gat gtg caa acg       528
Gly Arg Pro Gly Pro Val Trp Ile Asp Ile Pro Lys Asp Val Gln Thr
                165                 170                 175 gca gtt ttt gag att gaa aca cag ccc gct atg gca gaa aaa gcc gcc       576
Ala Val Phe Glu Ile Glu Thr Gln Pro Ala Met Ala Glu Lys Ala Ala
            180                 185                 190 gcc ccc gcc ttt agc gaa gaa agc att cgt gac gca gcg gcg atg att       624
Ala Pro Ala Phe Ser Glu Glu Ser Ile Arg Asp Ala Ala Ala Met Ile
        195                 200                 205 aac gct gcc aaa cgc ccg gtg ctt tat ctg ggc ggc ggt gtg atc aat       672
Asn Ala Ala Lys Arg Pro Val Leu Tyr Leu Gly Gly Gly Val Ile Asn
    210                 215                 220 gcg ccc gca cgg gtg cgt gaa ctg gcg gag aaa gcg caa ctg cct acc       720
Ala Pro Ala Arg Val Arg Glu Leu Ala Glu Lys Ala Gln Leu Pro Thr
225                 230                 235                 240 acc atg act tta atg gcg ctg ggc atg ttg cca aaa gcg cat ccg ttg       768
Thr Met Thr Leu Met Ala Leu Gly Met Leu Pro Lys Ala His Pro Leu
                245                 250                 255 tcg ctg ggt atg ctg ggg atg cac ggc gtg cgc agc acc aac tat att       816
Ser Leu Gly Met Leu Gly Met His Gly Val Arg Ser Thr Asn Tyr Ile
            260                 265                 270 ttg cag gag gcg gat ttg ttg ata gtg ctc ggt gcg cgt ttt gat gac       864
Leu Gln Glu Ala Asp Leu Leu Ile Val Leu Gly Ala Arg Phe Asp Asp
        275                 280                 285 cgg gcg att ggc aaa acc gag cag ttc tgt ccg aat gcc aaa atc att       912
Arg Ala Ile Gly Lys Thr Glu Gln Phe Cys Pro Asn Ala Lys Ile Ile
    290                 295                 300 cat gtc gat atc gac cgt gca gag ctg ggt aaa atc aag cag ccg cac       960
His Val Asp Ile Asp Arg Ala Glu Leu Gly Lys Ile Lys Gln Pro His
305                 310                 315                 320 gtg gcg att cag gcg gat gtt gat gac gtg ctg gcg cag ttg atc ccg      1008
Val Ala Ile Gln Ala Asp Val Asp Asp Val Leu Ala Gln Leu Ile Pro
                325                 330                 335 ctg gtg gaa gcg caa ccg cgt gca gag tgg cac cag ttg gta gcg gat      1056
Leu Val Glu Ala Gln Pro Arg Ala Glu Trp His Gln Leu Val Ala Asp
            340                 345                 350 ttg cag cgt gag ttt ccg tgt cca atc ccg aaa gcg tgc gat ccg tta      1104
Leu Gln Arg Glu Phe Pro Cys Pro Ile Pro Lys Ala Cys Asp Pro Leu
        355                 360                 365 agc cat tac ggc ctg atc aac gcc gtt gcc gcc tgt gtc gat gac aat      1152
```

```
Ser His Tyr Gly Leu Ile Asn Ala Val Ala Ala Cys Val Asp Asp Asn
    370                 375                 380 gca att atc acc acc gac gtt ggt cag cat cag atg tgg acc gcg caa      1200
Ala Ile Ile Thr Thr Asp Val Gly Gln His Gln Met Trp Thr Ala Gln
385                 390                 395                 400 gct tat ccg ctc aat cgc cca cgc cag tgg ctg acc tcc ggt ggg ctg      1248
Ala Tyr Pro Leu Asn Arg Pro Arg Gln Trp Leu Thr Ser Gly Gly Leu
                405                 410                 415 ggc acg atg ggt ttt ggc ctg cct gcg gcg att ggc gct gcg ctg gcg      1296
Gly Thr Met Gly Phe Gly Leu Pro Ala Ala Ile Gly Ala Ala Leu Ala
            420                 425                 430 aac ccg gat cgc aaa gtg ttg tgt ttc tcc ggc gac ggc agc ctg atg      1344
Asn Pro Asp Arg Lys Val Leu Cys Phe Ser Gly Asp Gly Ser Leu Met
        435                 440                 445 atg aat att cag gag atg gcg acc gcc agt gaa aat cag ctg gat gtc      1392
Met Asn Ile Gln Glu Met Ala Thr Ala Ser Glu Asn Gln Leu Asp Val
    450                 455                 460 aaa atc att ctg atg aac aac gaa gcg ctg ggg ctg gtg cat cag caa      1440
Lys Ile Ile Leu Met Asn Asn Glu Ala Leu Gly Leu Val His Gln Gln
465                 470                 475                 480 cag agt ctg ttc tac gag caa ggc gtt ttt gcc gcc acc tat ccg ggc      1488
Gln Ser Leu Phe Tyr Glu Gln Gly Val Phe Ala Ala Thr Tyr Pro Gly
                485                 490                 495 aaa atc aac ttt atg cag att gcc gcc gga ttc ggc ctc gaa acc tgt      1536
Lys Ile Asn Phe Met Gln Ile Ala Ala Gly Phe Gly Leu Glu Thr Cys
            500                 505                 510 gat ttg aat aac gaa gcc gat ccg cag gct tca ttg cag gaa atc atc      1584
Asp Leu Asn Asn Glu Ala Asp Pro Gln Ala Ser Leu Gln Glu Ile Ile
        515                 520                 525 aat cgc cct ggc ccg gcg ctg atc cat gtg cgc att gat gcc gaa gaa      1632
Asn Arg Pro Gly Pro Ala Leu Ile His Val Arg Ile Asp Ala Glu Glu
    530                 535                 540 aaa gtt tac ccg atg gtg ccg cca ggt gcg gcg aat act gaa atg gtg      1680
Lys Val Tyr Pro Met Val Pro Pro Gly Ala Ala Asn Thr Glu Met Val
545                 550                 555                 560 ggg gaa taa                                                            1689
Gly Glu <210> SEQ ID NO 2
<211> LENGTH: 562
<212> TYPE: PRT
<213> ORGANISM: Escherichia coli

<400> SEQUENCE: 2

Met Ala Ser Ser Gly Thr Thr Ser Thr Arg Lys Arg Phe Thr Gly Ala
1               5                   10                  15

Glu Phe Ile Val His Phe Leu Glu Gln Gln Gly Ile Lys Ile Val Thr
                20                  25                  30

Gly Ile Pro Gly Gly Ser Ile Leu Pro Val Tyr Asp Ala Leu Ser Gln
            35                  40                  45

Ser Thr Gln Ile Arg His Ile Leu Ala Arg His Glu Gln Gly Ala Gly
        50                  55                  60

Phe Ile Ala Gln Gly Met Ala Arg Thr Asp Gly Lys Pro Ala Val Cys
65                  70                  75                  80

Met Ala Cys Ser Gly Pro Gly Ala Thr Asn Leu Val Thr Ala Ile Ala
                85                  90                  95

Asp Ala Arg Leu Asp Ser Ile Pro Leu Ile Cys Ile Thr Gly Gln Val
            100                 105                 110
```

```
Pro Ala Ser Met Ile Gly Thr Asp Ala Phe Gln Glu Val Asp Thr Tyr
            115                 120                 125

Gly Ile Ser Ile Pro Ile Thr Lys His Asn Tyr Leu Val Arg His Ile
        130                 135                 140

Glu Glu Leu Pro Gln Val Met Ser Asp Ala Phe Arg Ile Ala Gln Ser
145                 150                 155                 160

Gly Arg Pro Gly Pro Val Trp Ile Asp Ile Pro Lys Asp Val Gln Thr
                165                 170                 175

Ala Val Phe Glu Ile Glu Thr Gln Pro Ala Met Ala Glu Lys Ala Ala
            180                 185                 190

Ala Pro Ala Phe Ser Glu Glu Ser Ile Arg Asp Ala Ala Met Ile
        195                 200                 205

Asn Ala Ala Lys Arg Pro Val Leu Tyr Leu Gly Gly Gly Val Ile Asn
    210                 215                 220

Ala Pro Ala Arg Val Arg Glu Leu Ala Glu Lys Ala Gln Leu Pro Thr
225                 230                 235                 240

Thr Met Thr Leu Met Ala Leu Gly Met Leu Pro Lys Ala His Pro Leu
                245                 250                 255

Ser Leu Gly Met Leu Gly Met His Gly Val Arg Ser Thr Asn Tyr Ile
            260                 265                 270

Leu Gln Glu Ala Asp Leu Leu Ile Val Leu Gly Ala Arg Phe Asp Asp
        275                 280                 285

Arg Ala Ile Gly Lys Thr Glu Gln Phe Cys Pro Asn Ala Lys Ile Ile
    290                 295                 300

His Val Asp Ile Asp Arg Ala Glu Leu Gly Lys Ile Lys Gln Pro His
305                 310                 315                 320

Val Ala Ile Gln Ala Asp Val Asp Val Leu Ala Gln Leu Ile Pro
                325                 330                 335

Leu Val Glu Ala Gln Pro Arg Ala Glu Trp His Gln Leu Val Ala Asp
            340                 345                 350

Leu Gln Arg Glu Phe Pro Cys Pro Ile Pro Lys Ala Cys Asp Pro Leu
        355                 360                 365

Ser His Tyr Gly Leu Ile Asn Ala Val Ala Ala Cys Val Asp Asp Asn
    370                 375                 380

Ala Ile Ile Thr Thr Asp Val Gly Gln His Gln Met Trp Thr Ala Gln
385                 390                 395                 400

Ala Tyr Pro Leu Asn Arg Pro Arg Gln Trp Leu Thr Ser Gly Gly Leu
                405                 410                 415

Gly Thr Met Gly Phe Gly Leu Pro Ala Ala Ile Gly Ala Ala Leu Ala
            420                 425                 430

Asn Pro Asp Arg Lys Val Leu Cys Phe Ser Gly Asp Gly Ser Leu Met
        435                 440                 445

Met Asn Ile Gln Glu Met Ala Thr Ala Ser Glu Asn Gln Leu Asp Val
    450                 455                 460

Lys Ile Ile Leu Met Asn Asn Glu Ala Leu Gly Leu Val His Gln Gln
465                 470                 475                 480

Gln Ser Leu Phe Tyr Glu Gln Gly Val Phe Ala Ala Thr Tyr Pro Gly
                485                 490                 495

Lys Ile Asn Phe Met Gln Ile Ala Ala Gly Phe Gly Leu Glu Thr Cys
            500                 505                 510

Asp Leu Asn Asn Glu Ala Asp Pro Gln Ala Ser Leu Gln Glu Ile Ile
        515                 520                 525

Asn Arg Pro Gly Pro Ala Leu Ile His Val Arg Ile Asp Ala Glu Glu
```

```
                 530                 535                 540

Lys Val Tyr Pro Met Val Pro Pro Gly Ala Ala Asn Thr Glu Met Val
545                 550                 555                 560

Gly Glu

<210> SEQ ID NO 3
<211> LENGTH: 291
<212> TYPE: DNA
<213> ORGANISM: Escherichia coli
<220> FEATURE:
<221> NAME/KEY: CDS
<222> LOCATION: (1)..(291)

<400> SEQUENCE: 3 atg caa aac aca act cat gac aac gta att ctg gag ctc acc gtt cgc      48
Met Gln Asn Thr Thr His Asp Asn Val Ile Leu Glu Leu Thr Val Arg
1               5                   10                  15 aac cat ccg ggc gta atg acc cac gtt tgt ggc ctt ttt gcc cgc cgc      96
Asn His Pro Gly Val Met Thr His Val Cys Gly Leu Phe Ala Arg Arg
                20                  25                  30 gct ttt aac gtt gaa ggc att ctt tgt ctg ccg att cag gac agc gac     144
Ala Phe Asn Val Glu Gly Ile Leu Cys Leu Pro Ile Gln Asp Ser Asp
            35                  40                  45 aaa agc cat atc tgg cta ctg gtc aat gac gac cag cgt ctg gag cag     192
Lys Ser His Ile Trp Leu Leu Val Asn Asp Asp Gln Arg Leu Glu Gln
        50                  55                  60 atg ata agc caa atc gat aag ctg gaa gat gtc gtg aaa gtg cag cgt     240
Met Ile Ser Gln Ile Asp Lys Leu Glu Asp Val Val Lys Val Gln Arg
65                  70                  75                  80 aat cag tcc gat ccg acg atg ttt aac aag atc gcg gtg ttt ttt cag     288
Asn Gln Ser Asp Pro Thr Met Phe Asn Lys Ile Ala Val Phe Phe Gln
                85                  90                  95 taa                                                                  291

<210> SEQ ID NO 4
<211> LENGTH: 96
<212> TYPE: PRT
<213> ORGANISM: Escherichia coli

<400> SEQUENCE: 4

Met Gln Asn Thr Thr His Asp Asn Val Ile Leu Glu Leu Thr Val Arg
1               5                   10                  15

Asn His Pro Gly Val Met Thr His Val Cys Gly Leu Phe Ala Arg Arg
                20                  25                  30

Ala Phe Asn Val Glu Gly Ile Leu Cys Leu Pro Ile Gln Asp Ser Asp
            35                  40                  45

Lys Ser His Ile Trp Leu Leu Val Asn Asp Asp Gln Arg Leu Glu Gln
        50                  55                  60

Met Ile Ser Gln Ile Asp Lys Leu Glu Asp Val Val Lys Val Gln Arg
65                  70                  75                  80

Asn Gln Ser Asp Pro Thr Met Phe Asn Lys Ile Ala Val Phe Phe Gln
                85                  90                  95

<210> SEQ ID NO 5
<211> LENGTH: 1725
<212> TYPE: DNA
<213> ORGANISM: Escherichia coli
<220> FEATURE:
<221> NAME/KEY: CDS
<222> LOCATION: (1)..(1725)
```

```
<400> SEQUENCE: 5 atg gag atg ttg tct gga gcc gag atg gtc gtc cga tcg ctt atc gat        48
Met Glu Met Leu Ser Gly Ala Glu Met Val Val Arg Ser Leu Ile Asp
1               5                   10                  15 cag ggc gtt aaa caa gta ttc ggt tat ccc gga ggc gca gtc ctt gat        96
Gln Gly Val Lys Gln Val Phe Gly Tyr Pro Gly Gly Ala Val Leu Asp
            20                  25                  30 att tat gat gca ttg cat acc gtg ggt ggt att gat cat gta tta gtt       144
Ile Tyr Asp Ala Leu His Thr Val Gly Gly Ile Asp His Val Leu Val
        35                  40                  45 cgt cat gag cag gcg gcg gtg cat atg gcc gat ggc ctg gcg cgc gcg       192
Arg His Glu Gln Ala Ala Val His Met Ala Asp Gly Leu Ala Arg Ala
50                  55                  60 acc ggg gaa gtc ggc gtc gtg ctg gta acg tcg ggt cca ggg gcg acc       240
Thr Gly Glu Val Gly Val Val Leu Val Thr Ser Gly Pro Gly Ala Thr
65                  70                  75                  80 aat gcg att act ggc atc gcc acc gct tat atg gat tcc att cca tta       288
Asn Ala Ile Thr Gly Ile Ala Thr Ala Tyr Met Asp Ser Ile Pro Leu
                85                  90                  95 gtt gtc ctt tcc ggg cag gta gcg acc tcg ttg ata ggt tac gat gcc       336
Val Val Leu Ser Gly Gln Val Ala Thr Ser Leu Ile Gly Tyr Asp Ala
            100                 105                 110 ttt cag gag tgc gac atg gtg ggg att tcg cga ccg gtg gtt aaa cac       384
Phe Gln Glu Cys Asp Met Val Gly Ile Ser Arg Pro Val Val Lys His
        115                 120                 125 agt ttt ctg gtt aag caa acg gaa gac att ccg cag gtg ctg aaa aag       432
Ser Phe Leu Val Lys Gln Thr Glu Asp Ile Pro Gln Val Leu Lys Lys
    130                 135                 140 gct ttc tgg ctg gcg gca agt ggt cgc cca gga cca gta gtc gtt gat       480
Ala Phe Trp Leu Ala Ala Ser Gly Arg Pro Gly Pro Val Val Val Asp
145                 150                 155                 160 tta ccg aaa gat att ctt aat ccg gcg aac aaa tta ccc tat gtc tgg       528
Leu Pro Lys Asp Ile Leu Asn Pro Ala Asn Lys Leu Pro Tyr Val Trp
                165                 170                 175 ccg gag tcg gtc agt atg cgt tct tac aat ccc act act acc gga cat       576
Pro Glu Ser Val Ser Met Arg Ser Tyr Asn Pro Thr Thr Thr Gly His
            180                 185                 190 aaa ggg caa att aag cgt gct ctg caa acg ctg gta gcg gca aaa aaa       624
Lys Gly Gln Ile Lys Arg Ala Leu Gln Thr Leu Val Ala Ala Lys Lys
        195                 200                 205 ccg gtt gtc tac gta ggc ggt ggg gca atc acg gcg ggc tgc cat cag       672
Pro Val Val Tyr Val Gly Gly Gly Ala Ile Thr Ala Gly Cys His Gln
    210                 215                 220 cag ttg aaa gaa acg gtg gag gcg ttg aat ctg ccc gtt gtt tgc tca       720
Gln Leu Lys Glu Thr Val Glu Ala Leu Asn Leu Pro Val Val Cys Ser
225                 230                 235                 240 ttg atg ggg ctg ggg gcg ttt ccg gca acg cat cgt cag gca ctg ggc       768
Leu Met Gly Leu Gly Ala Phe Pro Ala Thr His Arg Gln Ala Leu Gly
                245                 250                 255 atg ctg gga atg cac ggt acc tac gaa gcc aat atg acg atg cat aac       816
Met Leu Gly Met His Gly Thr Tyr Glu Ala Asn Met Thr Met His Asn
            260                 265                 270 gcg gat gtg att ttc gcc gtc ggg gta cga ttt gat gac cga acg acg       864
Ala Asp Val Ile Phe Ala Val Gly Val Arg Phe Asp Asp Arg Thr Thr
        275                 280                 285 aac aat ctg gca aag tac tgc cca aat gcc act gtt ctg cat atc gat       912
Asn Asn Leu Ala Lys Tyr Cys Pro Asn Ala Thr Val Leu His Ile Asp
    290                 295                 300 att gat cct act tcc att tct aaa acc gtg act gcg gat atc ccg att       960
```

```
Ile Asp Pro Thr Ser Ile Ser Lys Thr Val Thr Ala Asp Ile Pro Ile
305                 310                 315                 320 gtg ggg gat gct cgc cag gtc ctc gaa caa atg ctt gaa ctc ttg tcg        1008
Val Gly Asp Ala Arg Gln Val Leu Glu Gln Met Leu Glu Leu Leu Ser
                325                 330                 335 caa gaa tcc gcc cat caa cca ctg gat gag atc cgc gac tgg tgg cag        1056
Gln Glu Ser Ala His Gln Pro Leu Asp Glu Ile Arg Asp Trp Trp Gln
            340                 345                 350 caa att gaa cag tgg cgc gct cgt cag tgc ctg aaa tat gac act cac        1104
Gln Ile Glu Gln Trp Arg Ala Arg Gln Cys Leu Lys Tyr Asp Thr His
        355                 360                 365 agt gaa aag att aaa ccg cag gcg gtg atc gag act ctt tgg cgg ttg        1152
Ser Glu Lys Ile Lys Pro Gln Ala Val Ile Glu Thr Leu Trp Arg Leu
    370                 375                 380 acg aag gga gac gct tac gtg acg tcc gat gtc ggg cag cac cag atg        1200
Thr Lys Gly Asp Ala Tyr Val Thr Ser Asp Val Gly Gln His Gln Met
385                 390                 395                 400 ttt gct gca ctt tat tat cca ttc gac aaa ccg cgt cgc tgg atc aat        1248
Phe Ala Ala Leu Tyr Tyr Pro Phe Asp Lys Pro Arg Arg Trp Ile Asn
                405                 410                 415 tcc ggt ggc ctc ggc acg atg ggt ttt ggt tta cct gcg gca ctg ggc        1296
Ser Gly Gly Leu Gly Thr Met Gly Phe Gly Leu Pro Ala Ala Leu Gly
            420                 425                 430 gtc aaa atg gcg ttg cca gaa gaa acc gtg gtt tgc gtc act ggc gac        1344
Val Lys Met Ala Leu Pro Glu Glu Thr Val Val Cys Val Thr Gly Asp
        435                 440                 445 ggc agt att cag atg aac atc cag gaa ctg tct acc gcg ttg caa tac        1392
Gly Ser Ile Gln Met Asn Ile Gln Glu Leu Ser Thr Ala Leu Gln Tyr
    450                 455                 460 gag ttg ccc gta ctg gtg gtg aat ctc aat aac cgc tat ctg ggg atg        1440
Glu Leu Pro Val Leu Val Val Asn Leu Asn Asn Arg Tyr Leu Gly Met
465                 470                 475                 480 gtg aag cag tgg cag gac atg atc tat tcc ggc cgt cat tca caa tct        1488
Val Lys Gln Trp Gln Asp Met Ile Tyr Ser Gly Arg His Ser Gln Ser
                485                 490                 495 tat atg caa tcg cta ccc gat ttc gtc cgt ctg gcg gaa gcc tat ggg        1536
Tyr Met Gln Ser Leu Pro Asp Phe Val Arg Leu Ala Glu Ala Tyr Gly
            500                 505                 510 cat gtc ggg atc cag att tct cat ccg cat gag ctg gaa agc aaa ctt        1584
His Val Gly Ile Gln Ile Ser His Pro His Glu Leu Glu Ser Lys Leu
        515                 520                 525 agc gag gcg ctg gaa cag gtg cgc aat aat cgc ctg gtg ttt gtt gat        1632
Ser Glu Ala Leu Glu Gln Val Arg Asn Asn Arg Leu Val Phe Val Asp
    530                 535                 540 gtt acc gtc gat ggc agc gag cac gtc tac ccg atg cag att cgc ggg        1680
Val Thr Val Asp Gly Ser Glu His Val Tyr Pro Met Gln Ile Arg Gly
545                 550                 555                 560 ggc gga atg gat gaa atg tgg tta agc aaa acg gag aga acc tga            1725
Gly Gly Met Asp Glu Met Trp Leu Ser Lys Thr Glu Arg Thr
                565                 570

<210> SEQ ID NO 6
<211> LENGTH: 574
<212> TYPE: PRT
<213> ORGANISM: Escherichia coli

<400> SEQUENCE: 6

Met Glu Met Leu Ser Gly Ala Glu Met Val Val Arg Ser Leu Ile Asp
1               5                   10                  15

Gln Gly Val Lys Gln Val Phe Gly Tyr Pro Gly Gly Ala Val Leu Asp
```

```
            20                  25                  30
Ile Tyr Asp Ala Leu His Thr Val Gly Gly Ile Asp His Val Leu Val
            35                  40                  45

Arg His Glu Gln Ala Ala Val His Met Ala Asp Gly Leu Ala Arg Ala
 50                  55                  60

Thr Gly Glu Val Gly Val Leu Val Thr Ser Pro Gly Ala Thr
 65                  70                  75                  80

Asn Ala Ile Thr Gly Ile Ala Thr Ala Tyr Met Asp Ser Ile Pro Leu
                    85                  90                  95

Val Val Leu Ser Gly Gln Val Ala Thr Ser Leu Ile Gly Tyr Asp Ala
                100                 105                 110

Phe Gln Glu Cys Asp Met Val Gly Ile Ser Arg Pro Val Val Lys His
                115                 120                 125

Ser Phe Leu Val Lys Gln Thr Glu Asp Ile Pro Gln Val Leu Lys Lys
                130                 135                 140

Ala Phe Trp Leu Ala Ala Ser Gly Arg Pro Gly Pro Val Val Val Asp
145                 150                 155                 160

Leu Pro Lys Asp Ile Leu Asn Pro Ala Asn Lys Leu Pro Tyr Val Trp
                165                 170                 175

Pro Glu Ser Val Ser Met Arg Ser Tyr Asn Pro Thr Thr Thr Gly His
                180                 185                 190

Lys Gly Gln Ile Lys Arg Ala Leu Gln Thr Leu Val Ala Ala Lys Lys
                195                 200                 205

Pro Val Val Tyr Val Gly Gly Gly Ala Ile Thr Ala Gly Cys His Gln
                210                 215                 220

Gln Leu Lys Glu Thr Val Glu Ala Leu Asn Leu Pro Val Val Cys Ser
225                 230                 235                 240

Leu Met Gly Leu Gly Ala Phe Pro Ala Thr His Arg Gln Ala Leu Gly
                245                 250                 255

Met Leu Gly Met His Gly Thr Tyr Glu Ala Asn Met Thr Met His Asn
                260                 265                 270

Ala Asp Val Ile Phe Ala Val Gly Val Arg Phe Asp Asp Arg Thr Thr
                275                 280                 285

Asn Asn Leu Ala Lys Tyr Cys Pro Asn Ala Thr Val Leu His Ile Asp
                290                 295                 300

Ile Asp Pro Thr Ser Ile Ser Lys Thr Val Thr Ala Asp Ile Pro Ile
305                 310                 315                 320

Val Gly Asp Ala Arg Gln Val Leu Glu Gln Met Leu Glu Leu Leu Ser
                325                 330                 335

Gln Glu Ser Ala His Gln Pro Leu Asp Glu Ile Arg Asp Trp Trp Gln
                340                 345                 350

Gln Ile Glu Gln Trp Arg Ala Arg Gln Cys Leu Lys Tyr Asp Thr His
                355                 360                 365

Ser Glu Lys Ile Lys Pro Gln Ala Val Ile Glu Thr Leu Trp Arg Leu
                370                 375                 380

Thr Lys Gly Asp Ala Tyr Val Thr Ser Asp Val Gly Gln His Gln Met
385                 390                 395                 400

Phe Ala Ala Leu Tyr Tyr Pro Phe Asp Lys Pro Arg Arg Trp Ile Asn
                405                 410                 415

Ser Gly Gly Leu Gly Thr Met Gly Phe Gly Leu Pro Ala Ala Leu Gly
                420                 425                 430

Val Lys Met Ala Leu Pro Glu Glu Thr Val Val Cys Val Thr Gly Asp
                435                 440                 445
```

```
Gly Ser Ile Gln Met Asn Ile Gln Glu Leu Ser Thr Ala Leu Gln Tyr
        450                 455                 460

Glu Leu Pro Val Leu Val Asn Leu Asn Asn Arg Tyr Leu Gly Met
465             470                 475                 480

Val Lys Gln Trp Gln Asp Met Ile Tyr Ser Gly Arg His Ser Gln Ser
                    485                 490                 495

Tyr Met Gln Ser Leu Pro Asp Phe Val Arg Leu Ala Glu Ala Tyr Gly
            500                 505                 510

His Val Gly Ile Gln Ile Ser His Pro His Glu Leu Glu Ser Lys Leu
            515                 520                 525

Ser Glu Ala Leu Glu Gln Val Arg Asn Asn Arg Leu Val Phe Val Asp
        530                 535                 540

Val Thr Val Asp Gly Ser Glu His Val Tyr Pro Met Gln Ile Arg Gly
545                 550                 555                 560

Gly Gly Met Asp Glu Met Trp Leu Ser Lys Thr Glu Arg Thr
                565                 570
```

<210> SEQ ID NO 7
<211> LENGTH: 492
<212> TYPE: DNA
<213> ORGANISM: Escherichia coli
<220> FEATURE:
<221> NAME/KEY: CDS
<222> LOCATION: (1)..(492)

<400> SEQUENCE: 7

```
atg cgc cgg ata tta tca gtc tta ctc gaa aat gaa tca ggc gcg tta         48
Met Arg Arg Ile Leu Ser Val Leu Leu Glu Asn Glu Ser Gly Ala Leu
1               5                   10                  15 tcc cgc gtg att ggc ctt ttt tcc cag cgt ggc tac aac att gaa agc         96
Ser Arg Val Ile Gly Leu Phe Ser Gln Arg Gly Tyr Asn Ile Glu Ser
            20                  25                  30 ctg acc gtt gcg cca acc gac gat ccg aca tta tcg cgt atg acc atc        144
Leu Thr Val Ala Pro Thr Asp Asp Pro Thr Leu Ser Arg Met Thr Ile
        35                  40                  45 cag acc gtg ggc gat gaa aaa gta ctt gag cag atc gaa aag caa tta        192
Gln Thr Val Gly Asp Glu Lys Val Leu Glu Gln Ile Glu Lys Gln Leu
    50                  55                  60 cac aaa ctg gtc gat gtc ttg cgc gtg agt gag ttg ggg cag ggc gcg        240
His Lys Leu Val Asp Val Leu Arg Val Ser Glu Leu Gly Gln Gly Ala
65                  70                  75                  80 cat gtt gag cgg gaa atc atg ctg gtg aaa att cag gcc agc ggt tac        288
His Val Glu Arg Glu Ile Met Leu Val Lys Ile Gln Ala Ser Gly Tyr
                85                  90                  95 ggg cgt gac gaa gtg aaa cgt aat acg gaa ata ttc cgt ggg caa att        336
Gly Arg Asp Glu Val Lys Arg Asn Thr Glu Ile Phe Arg Gly Gln Ile
            100                 105                 110 atc gat gtc aca ccc tcg ctt tat acc gtt caa tta gca ggc acc agc        384
Ile Asp Val Thr Pro Ser Leu Tyr Thr Val Gln Leu Ala Gly Thr Ser
        115                 120                 125 ggt aag ctt gat gca ttt tta gca tcg att cgc gat gtg gcg aaa att        432
Gly Lys Leu Asp Ala Phe Leu Ala Ser Ile Arg Asp Val Ala Lys Ile
    130                 135                 140 gtg gag gtt gct cgc tct ggt gtg gtc gga ctt tcg cgc ggc gat aaa        480
Val Glu Val Ala Arg Ser Gly Val Val Gly Leu Ser Arg Gly Asp Lys
145                 150                 155                 160 ata atg cgt tga                                                        492
Ile Met Arg
```

<210> SEQ ID NO 8
<211> LENGTH: 163
<212> TYPE: PRT
<213> ORGANISM: Escherichia coli

<400> SEQUENCE: 8

```
Met Arg Arg Ile Leu Ser Val Leu Leu Glu Asn Glu Ser Gly Ala Leu
1               5                   10                  15

Ser Arg Val Ile Gly Leu Phe Ser Gln Arg Gly Tyr Asn Ile Glu Ser
            20                  25                  30

Leu Thr Val Ala Pro Thr Asp Asp Pro Thr Leu Ser Arg Met Thr Ile
        35                  40                  45

Gln Thr Val Gly Asp Glu Lys Val Leu Glu Gln Ile Glu Lys Gln Leu
50                  55                  60

His Lys Leu Val Asp Val Leu Arg Val Ser Glu Leu Gly Gln Gly Ala
65                  70                  75                  80

His Val Glu Arg Glu Ile Met Leu Val Lys Ile Gln Ala Ser Gly Tyr
                85                  90                  95

Gly Arg Asp Glu Val Lys Arg Asn Thr Glu Ile Phe Arg Gly Gln Ile
            100                 105                 110

Ile Asp Val Thr Pro Ser Leu Tyr Thr Val Gln Leu Ala Gly Thr Ser
        115                 120                 125

Gly Lys Leu Asp Ala Phe Leu Ala Ser Ile Arg Asp Val Ala Lys Ile
130                 135                 140

Val Glu Val Ala Arg Ser Gly Val Val Gly Leu Ser Arg Gly Asp Lys
145                 150                 155                 160

Ile Met Arg
```

<210> SEQ ID NO 9
<211> LENGTH: 894
<212> TYPE: DNA
<213> ORGANISM: Escherichia coli
<220> FEATURE:
<221> NAME/KEY: CDS
<222> LOCATION: (1)..(894)

<400> SEQUENCE: 9

```
gtg gat tta cgc gat ctg aaa acc ttc ctg cat ctg gcg gaa agc cgc    48
Val Asp Leu Arg Asp Leu Lys Thr Phe Leu His Leu Ala Glu Ser Arg
1               5                   10                  15 cat ttt ggc cgc agc gcg cgg gcg atg cac gtt agc cca tcc acg ctc    96
His Phe Gly Arg Ser Ala Arg Ala Met His Val Ser Pro Ser Thr Leu
            20                  25                  30 tca cgg cag att cag cgc ctg gaa gaa gat ctc ggt cag ccg ctg ttt   144
Ser Arg Gln Ile Gln Arg Leu Glu Glu Asp Leu Gly Gln Pro Leu Phe
        35                  40                  45 gtg cgc gat aac cgc acg gtg acg ctg act gaa gcg ggc gaa gag ctg   192
Val Arg Asp Asn Arg Thr Val Thr Leu Thr Glu Ala Gly Glu Glu Leu
50                  55                  60 cgc gtt ttc gcc cag caa acg ctg ttg cag tat cag cag ttg cgc cac   240
Arg Val Phe Ala Gln Gln Thr Leu Leu Gln Tyr Gln Gln Leu Arg His
65                  70                  75                  80 acc atc gat cag caa ggg ccg tcg ctc tct ggc gaa tta cat atc ttc   288
Thr Ile Asp Gln Gln Gly Pro Ser Leu Ser Gly Glu Leu His Ile Phe
                85                  90                  95 tgc tcg gtg acc gct gcc tac agc cat ctg ccg ccg att ctg gat cgc   336
Cys Ser Val Thr Ala Ala Tyr Ser His Leu Pro Pro Ile Leu Asp Arg
            100                 105                 110
```

```
ttc cgc gcg gaa cac ccg tcg gtg gag att aaa ctt act act ggt gat    384
Phe Arg Ala Glu His Pro Ser Val Glu Ile Lys Leu Thr Thr Gly Asp
        115                 120                 125 gcg gca gat gcg atg gaa aag gtg gtc act ggt gaa gcg gat ctg gcg    432
Ala Ala Asp Ala Met Glu Lys Val Val Thr Gly Glu Ala Asp Leu Ala
    130                 135                 140 att gcg ggt aaa ccg gaa acc ttg ccc ggc gca gtg gcg ttt tcg atg    480
Ile Ala Gly Lys Pro Glu Thr Leu Pro Gly Ala Val Ala Phe Ser Met
145                 150                 155                 160 ctg gag aat ctg gca gta gtg ctg att gcc ccc gcg ctg ccc tgc ccg    528
Leu Glu Asn Leu Ala Val Val Leu Ile Ala Pro Ala Leu Pro Cys Pro
                165                 170                 175 gtg cgt aat cag gtg tcg gta gag aag ccg gac tgg tca acg gtg ccg    576
Val Arg Asn Gln Val Ser Val Glu Lys Pro Asp Trp Ser Thr Val Pro
            180                 185                 190 ttt att atg gcc gat cag ggg ccg gta cgc cgc cgc att gaa ctg tgg    624
Phe Ile Met Ala Asp Gln Gly Pro Val Arg Arg Arg Ile Glu Leu Trp
        195                 200                 205 ttt cga cgc aat aaa atc agt aac ccg atg att tac gcc acg gtt ggc    672
Phe Arg Arg Asn Lys Ile Ser Asn Pro Met Ile Tyr Ala Thr Val Gly
    210                 215                 220 ggg cat gaa gcg atg gta tcg atg gtg gca ctc ggc tgt ggc gtg gca    720
Gly His Glu Ala Met Val Ser Met Val Ala Leu Gly Cys Gly Val Ala
225                 230                 235                 240 ttg ttg ccg gaa gtg gtg ctg gaa aac agc ccc gaa ccg gtg cgt aac    768
Leu Leu Pro Glu Val Val Leu Glu Asn Ser Pro Glu Pro Val Arg Asn
                245                 250                 255 cgc gtg atg att tta gag cgc agc gat gag aaa acg ccg ttt gag ctg    816
Arg Val Met Ile Leu Glu Arg Ser Asp Glu Lys Thr Pro Phe Glu Leu
            260                 265                 270 ggc gtg tgt gcg cag aaa aag cgg cta cat gag ccg cta att gag gca    864
Gly Val Cys Ala Gln Lys Lys Arg Leu His Glu Pro Leu Ile Glu Ala
        275                 280                 285 ttc tgg aag att ttg ccg aac cac aaa tga                            894
Phe Trp Lys Ile Leu Pro Asn His Lys
    290                 295

<210> SEQ ID NO 10
<211> LENGTH: 297
<212> TYPE: PRT
<213> ORGANISM: Escherichia coli

<400> SEQUENCE: 10

Met Asp Leu Arg Asp Leu Lys Thr Phe Leu His Leu Ala Glu Ser Arg
1               5                   10                  15

His Phe Gly Arg Ser Ala Arg Ala Met His Val Ser Pro Ser Thr Leu
            20                  25                  30

Ser Arg Gln Ile Gln Arg Leu Glu Glu Asp Leu Gly Gln Pro Leu Phe
        35                  40                  45

Val Arg Asp Asn Arg Thr Val Thr Leu Thr Glu Ala Gly Glu Glu Leu
    50                  55                  60

Arg Val Phe Ala Gln Gln Thr Leu Leu Gln Tyr Gln Gln Leu Arg His
65                  70                  75                  80

Thr Ile Asp Gln Gln Gly Pro Ser Leu Ser Gly Glu Leu His Ile Phe
                85                  90                  95

Cys Ser Val Thr Ala Ala Tyr Ser His Leu Pro Pro Ile Leu Asp Arg
            100                 105                 110

Phe Arg Ala Glu His Pro Ser Val Glu Ile Lys Leu Thr Thr Gly Asp
        115                 120                 125
```

```
Ala Ala Asp Ala Met Glu Lys Val Val Thr Gly Glu Ala Asp Leu Ala
        130                 135                 140

Ile Ala Gly Lys Pro Glu Thr Leu Pro Gly Ala Val Ala Phe Ser Met
145                 150                 155                 160

Leu Glu Asn Leu Ala Val Val Leu Ile Ala Pro Ala Leu Pro Cys Pro
                165                 170                 175

Val Arg Asn Gln Val Ser Val Glu Lys Pro Asp Trp Ser Thr Val Pro
            180                 185                 190

Phe Ile Met Ala Asp Gln Gly Pro Val Arg Arg Ile Glu Leu Trp
        195                 200                 205

Phe Arg Arg Asn Lys Ile Ser Asn Pro Met Ile Tyr Ala Thr Val Gly
    210                 215                 220

Gly His Glu Ala Met Val Ser Met Val Ala Leu Gly Cys Gly Val Ala
225                 230                 235                 240

Leu Leu Pro Glu Val Val Leu Glu Asn Ser Pro Glu Pro Val Arg Asn
                245                 250                 255

Arg Val Met Ile Leu Glu Arg Ser Asp Glu Lys Thr Pro Phe Glu Leu
            260                 265                 270

Gly Val Cys Ala Gln Lys Lys Arg Leu His Glu Pro Leu Ile Glu Ala
        275                 280                 285

Phe Trp Lys Ile Leu Pro Asn His Lys
    290                 295

<210> SEQ ID NO 11
<211> LENGTH: 64
<212> TYPE: DNA
<213> ORGANISM: Artificial Sequence
<220> FEATURE:
<223> OTHER INFORMATION: primer P1

<400> SEQUENCE: 11
gagctgggct acgattgcca cgacgaaacc aataactgaa gcctgctttt ttatactaag   60
ttgg                                                                64

<210> SEQ ID NO 12
<211> LENGTH: 64
<212> TYPE: DNA
<213> ORGANISM: Artificial Sequence
<220> FEATURE:
<223> OTHER INFORMATION: primer P2

<400> SEQUENCE: 12
ttttccctaa cccgccaaaa agaacctgaa cgccggcgct caagttagta taaaaaagct   60
gaac                                                                64

<210> SEQ ID NO 13
<211> LENGTH: 64
<212> TYPE: DNA
<213> ORGANISM: Artificial Sequence
<220> FEATURE:
<223> OTHER INFORMATION: primer P3

<400> SEQUENCE: 13
ttgtgagcgg ataacaattt cacacaggaa acagcttgaa gcctgctttt ttatactaag   60
ttgg                                                                64

<210> SEQ ID NO 14
<211> LENGTH: 64
```

```
<212> TYPE: DNA
<213> ORGANISM: Artificial Sequence
<220> FEATURE:
<223> OTHER INFORMATION: primer P4

<400> SEQUENCE: 14
taaaacgacg gccagtgaat ccgtaatcat ggtcatggtg attcctcgtg atgttgtgct    60
tctt                                                                 64

<210> SEQ ID NO 15
<211> LENGTH: 64
<212> TYPE: DNA
<213> ORGANISM: Artificial Sequence
<220> FEATURE:
<223> OTHER INFORMATION: primer P5

<400> SEQUENCE: 15
gaccggcccg ctgcacaccc agttcggata tcacatcgct caagttagta taaaaagct     60 gaac                                                                 64

<210> SEQ ID NO 16
<211> LENGTH: 64
<212> TYPE: DNA
<213> ORGANISM: Artificial Sequence
<220> FEATURE:
<223> OTHER INFORMATION: primer P6

<400> SEQUENCE: 16
gctgggctac gattgccacg acgaaaccaa taaccctgaa gcctgctttt ttatactaag    60
ttgg                                                                 64

<210> SEQ ID NO 17
<211> LENGTH: 64
<212> TYPE: DNA
<213> ORGANISM: Artificial Sequence
<220> FEATURE:
<223> OTHER INFORMATION: primer P7

<400> SEQUENCE: 17
atgttgtgcc cgaacttgcc atgctccagt ctccttggtg attcctcgtg atgttgtgct    60
tctt                                                                 64

<210> SEQ ID NO 18
<211> LENGTH: 64
<212> TYPE: DNA
<213> ORGANISM: Artificial Sequence
<220> FEATURE:
<223> OTHER INFORMATION: primer P8

<400> SEQUENCE: 18
ccgcaggcga ctgacgaaac ctcgctccgg cggggttgaa gcctgctttt ttatactaag    60
ttgg                                                                 64

<210> SEQ ID NO 19
<211> LENGTH: 64
<212> TYPE: DNA
<213> ORGANISM: Artificial Sequence
<220> FEATURE:
<223> OTHER INFORMATION: primer eP9

<400> SEQUENCE: 19
acgtcaacat cgagggctgt ccctgtggat ttacgctgaa gcctgctttt ttatactaag    60
``` ttgg                                                              64

<210> SEQ ID NO 20
<211> LENGTH: 64
<212> TYPE: DNA
<213> ORGANISM: Artificial Sequence
<220> FEATURE:
<223> OTHER INFORMATION: primer P10

<400> SEQUENCE: 20
ggcggctttc cgccagatgc aggaaggttt tcagatcgct caagttagta taaaaaagct   60
gaac                                                              64

<210> SEQ ID NO 21
<211> LENGTH: 18
<212> TYPE: DNA
<213> ORGANISM: Artificial Sequence
<220> FEATURE:
<223> OTHER INFORMATION: primer P11

<400> SEQUENCE: 21
gctgaatctg ccgtgaga                                               18

<210> SEQ ID NO 22
<211> LENGTH: 18
<212> TYPE: DNA
<213> ORGANISM: Artificial Sequence
<220> FEATURE:
<223> OTHER INFORMATION: primer P12

<400> SEQUENCE: 22
ctggcgcaga ttcagtgt                                               18

<210> SEQ ID NO 23
<211> LENGTH: 17
<212> TYPE: DNA
<213> ORGANISM: Artificial Sequence
<220> FEATURE:
<223> OTHER INFORMATION: primer P13

<400> SEQUENCE: 23
tggcacgaca ggtttcc                                                17

<210> SEQ ID NO 24
<211> LENGTH: 18
<212> TYPE: DNA
<213> ORGANISM: Artificial Sequence
<220> FEATURE:
<223> OTHER INFORMATION: primer P14

<400> SEQUENCE: 24
gcctcttcgc tattacgc                                               18

<210> SEQ ID NO 25
<211> LENGTH: 21
<212> TYPE: DNA
<213> ORGANISM: Artificial Sequence
<220> FEATURE:
<223> OTHER INFORMATION: primer P15

<400> SEQUENCE: 25
ttgttccact atcgcagcca t                                           21

<210> SEQ ID NO 26
<211> LENGTH: 21

```
<212> TYPE: DNA
<213> ORGANISM: Artificial Sequence
<220> FEATURE:
<223> OTHER INFORMATION: primer P16

<400> SEQUENCE: 26
atggttccgg cgttcgataa a                                               21

<210> SEQ ID NO 27
<211> LENGTH: 20
<212> TYPE: DNA
<213> ORGANISM: Artificial Sequence
<220> FEATURE:
<223> OTHER INFORMATION: primer P17

<400> SEQUENCE: 27
agtgtgcttt gcggttacca                                                 20

<210> SEQ ID NO 28
<211> LENGTH: 20
<212> TYPE: DNA
<213> ORGANISM: Artificial Sequence
<220> FEATURE:
<223> OTHER INFORMATION: primer P18

<400> SEQUENCE: 28
tgccatgctc cagtctcctt                                                 20

<210> SEQ ID NO 29
<211> LENGTH: 20
<212> TYPE: DNA
<213> ORGANISM: Artificial Sequence
<220> FEATURE:
<223> OTHER INFORMATION: primer P19

<400> SEQUENCE: 29
gtaaagcgct tacgcgtcga                                                 20

<210> SEQ ID NO 30
<211> LENGTH: 85
<212> TYPE: DNA
<213> ORGANISM: Escherichia coli

<400> SEQUENCE: 30
attgcaatgt gacgttgtga atatatcaat ttccgcaata aatttcctgt catatagtga     60
attcaatctc gcaaacgcga accga                                           85

<210> SEQ ID NO 31
<211> LENGTH: 1647
<212> TYPE: DNA
<213> ORGANISM: Escherichia coli

<400> SEQUENCE: 31
atgaatggcg cacagtgggt ggtacatgcg ttgcgggcac agggtgtgaa caccgttttc     60
ggttatccgg gtggcgcaat tatgccggtt tacgatgcat tgtatgacgg cggcgtggag    120
cacttgctat gccgacatga gcagggtgcg gcaatggcgg ctatcggtta tgctcgtgct    180
accggcaaaa ctggcgtatg tatcgccacg tctggtccgg gcgcaaccaa cctgataacc    240
gggcttgcgg acgcactgtt agattccatc cctgttgttg ccatcaccgg tcaagtgtcc    300
gcaccgttta tcggcactga cgcatttcag gaagtggatg tcctgggatt gtcgttagcc    360
tgtaccaagc acagctttct ggtgcagtcg ctggaagagt tgccgcgcat catggctgaa    420
```

```
gcattcgacg ttgcctgctc aggtcgtcct ggtccggttc tggtcgatat cccaaaagat      480
atccagttag ccagcggtga cctggaaccg tggttcacca ccgttgaaaa cgaagtgact      540
ttcccacatg ccgaagttga gcaagcgcgc cagatgctgg caaaagcgca aaaaccgatg      600
ctgtacgttg gcggtggcgt gggtatggcg caggcagttc cggctttgcg tgaatttctc      660
gctgccacaa aaatgcctgc cacctgtacg ctgaaagggc tgggcgcagt agaagcagat      720
tatccgtact atctgggcat gctggggatg cacggcacca aagcggcaaa cttcgcggtg      780
caggagtgtg acctgctgat cgccgtgggc gcacgttttg atgaccgggt gaccggcaaa      840
ctgaacacct tcgcgccaca cgccagtgtt atccatatgg atatcgaccc ggcagaaatg      900
aacaagctgc gtcaggcaca tgtggcatta caaggtgatt aaatgctctg ttaccagca       960
ttacagcagc cgttaaatca atgagactgg cagcaacact gcgcgcagct gcgtgatgaa      1020
cattcctggc gttacgacca tcccggtgac gctatctacg cgccgttgtt gttaaaacaa      1080
ctgtcggatc gtaaacctgc ggattgcgtc gtgaccacag atgtggggca gcaccagatg      1140
tgggctgcgc agcacatcgc ccacactcgc ccggaaaatt tcatcacctc agcggtttta      1200
ggtaccatgg gttttggttt accggcggcg gttggcgcac aagtcgcgcg accgaacgat      1260
accgttgtct gtatctccgg tgacggctct ttcatgatga atgtgcaaga gctgggcacc      1320
gtaaaacgca agcagttacc gttgaaaatc gtcttactcg ataaccaacg gttagggatg      1380
gttcgacaat ggcagcaact gttttttcag aacgataca gcgaaaccac ccttactgat       1440
aaccccgatt tcctcatgtt agccagcgcc ttcggcatcc atggccaaca catcacccgg      1500
aaagaccagg ttgaagcggc actcgacacc atgctgaaca gtgatgggcc ataccctgctt     1560
catgtctcaa tcgacgaact tgagaacgtc tggccgctgg tgccgcctgg cgccagtaat      1620
tcagaaatgt tggagaaatt atcatga                                          1647

<210> SEQ ID NO 32
<211> LENGTH: 548
<212> TYPE: PRT
<213> ORGANISM: Artificial Sequence
<220> FEATURE:
<223> OTHER INFORMATION: IlvG PR

<400> SEQUENCE: 32

Met Asn Gly Ala Gln Trp Val Val His Ala Leu Arg Ala Gln Gly Val
1               5                   10                  15

Asn Thr Val Phe Gly Tyr Pro Gly Gly Ala Ile Met Pro Val Tyr Asp
            20                  25                  30

Ala Leu Tyr Asp Gly Gly Val Glu His Leu Leu Cys Arg His Glu Gln
        35                  40                  45

Gly Ala Ala Met Ala Ala Ile Gly Tyr Ala Arg Ala Thr Gly Lys Thr
    50                  55                  60

Gly Val Cys Ile Ala Thr Ser Gly Pro Gly Ala Thr Asn Leu Ile Thr
65                  70                  75                  80

Gly Leu Ala Asp Ala Leu Leu Asp Ser Ile Pro Val Val Ala Ile Thr
                85                  90                  95

Gly Gln Val Ser Ala Pro Phe Ile Gly Thr Asp Ala Phe Gln Glu Val
            100                 105                 110

Asp Val Leu Gly Leu Ser Leu Ala Cys Thr Lys His Ser Phe Leu Val
        115                 120                 125

Gln Ser Leu Glu Glu Leu Pro Arg Ile Met Ala Glu Ala Phe Asp Val
    130                 135                 140
```

```
Ala Cys Ser Gly Arg Pro Gly Pro Val Leu Val Asp Ile Pro Lys Asp
145                 150                 155                 160

Ile Gln Leu Ala Ser Gly Asp Leu Glu Pro Trp Phe Thr Thr Val Glu
            165                 170                 175

Asn Glu Val Thr Phe Pro His Ala Glu Val Glu Gln Ala Arg Gln Met
        180                 185                 190

Leu Ala Lys Ala Gln Lys Pro Met Leu Tyr Val Gly Gly Gly Val Gly
    195                 200                 205

Met Ala Gln Ala Val Pro Ala Leu Arg Glu Phe Leu Ala Ala Thr Lys
    210                 215                 220

Met Pro Ala Thr Cys Thr Leu Lys Gly Leu Gly Ala Val Glu Ala Asp
225                 230                 235                 240

Tyr Pro Tyr Tyr Leu Gly Met Leu Gly Met His Gly Thr Lys Ala Ala
                245                 250                 255

Asn Phe Ala Val Gln Glu Cys Asp Leu Leu Ile Ala Val Gly Ala Arg
                260                 265                 270

Phe Asp Asp Arg Val Thr Gly Lys Leu Asn Thr Phe Ala Pro His Ala
            275                 280                 285

Ser Val Ile His Met Asp Ile Asp Pro Ala Glu Met Asn Lys Leu Arg
        290                 295                 300

Gln Ala His Val Ala Leu Gln Gly Asp Leu Asn Ala Leu Leu Pro Ala
305                 310                 315                 320

Leu Gln Gln Pro Leu Asn Gln Asn Asp Trp Gln His Cys Ala Gln
                325                 330                 335

Leu Arg Asp Glu His Ser Trp Arg Tyr Asp His Pro Gly Asp Ala Ile
                340                 345                 350

Tyr Ala Pro Leu Leu Leu Lys Gln Leu Ser Asp Arg Lys Pro Ala Asp
            355                 360                 365

Cys Val Val Thr Thr Asp Val Gly Gln His Gln Met Trp Ala Ala Gln
370                 375                 380

His Ile Ala His Thr Arg Pro Glu Asn Phe Ile Thr Ser Ser Gly Leu
385                 390                 395                 400

Gly Thr Met Gly Phe Gly Leu Pro Ala Ala Val Gly Ala Gln Val Ala
                405                 410                 415

Arg Pro Asn Asp Thr Val Val Cys Ile Ser Gly Asp Gly Ser Phe Met
            420                 425                 430

Met Asn Val Gln Glu Leu Gly Thr Val Lys Arg Lys Gln Leu Pro Leu
            435                 440                 445

Lys Ile Val Leu Leu Asp Asn Gln Arg Leu Gly Met Val Arg Gln Trp
450                 455                 460

Gln Gln Leu Phe Phe Gln Glu Arg Tyr Ser Glu Thr Thr Leu Thr Asp
465                 470                 475                 480

Asn Pro Asp Phe Leu Met Leu Ala Ser Ala Phe Gly Ile His Gly Gln
            485                 490                 495

His Ile Thr Arg Lys Asp Gln Val Glu Ala Ala Leu Asp Thr Met Leu
            500                 505                 510

Asn Ser Asp Gly Pro Tyr Leu Leu His Val Ser Ile Asp Glu Leu Glu
            515                 520                 525

Asn Val Trp Pro Leu Val Pro Pro Gly Ala Ser Asn Ser Glu Met Leu
            530                 535                 540

Glu Lys Leu Ser
545
```

```
<210> SEQ ID NO 33
<211> LENGTH: 264
<212> TYPE: DNA
<213> ORGANISM: Escherichia coli
<220> FEATURE:
<221> NAME/KEY: CDS
<222> LOCATION: (1)..(264)

<400> SEQUENCE: 33 atg atg caa cat cag gtc aat gta tcg gct cgc ttc aat cca gaa acc        48
Met Met Gln His Gln Val Asn Val Ser Ala Arg Phe Asn Pro Glu Thr
1               5                  10                  15 tta gaa cgt gtt tta cgc gtg gtg cgt cat cgt ggt ttc cac gtc tgc        96
Leu Glu Arg Val Leu Arg Val Val Arg His Arg Gly Phe His Val Cys
            20                  25                  30 tca atg aat atg gcc gcc gcc agc gat gca caa aat ata aat atc gaa       144
Ser Met Asn Met Ala Ala Ala Ser Asp Ala Gln Asn Ile Asn Ile Glu
        35                  40                  45 ttg acc gtt gcc agc cca cgg tcg gtc gac tta ctg ttt agt cag tta       192
Leu Thr Val Ala Ser Pro Arg Ser Val Asp Leu Leu Phe Ser Gln Leu
    50                  55                  60 aat aaa ctg gtg gac gtc gca cac gtt gcc atc tgc cag agc aca acc       240
Asn Lys Leu Val Asp Val Ala His Val Ala Ile Cys Gln Ser Thr Thr
65                  70                  75                  80 aca tca caa caa atc cgc gcc tga                                        264
Thr Ser Gln Gln Ile Arg Ala
                85

<210> SEQ ID NO 34
<211> LENGTH: 87
<212> TYPE: PRT
<213> ORGANISM: Escherichia coli

<400> SEQUENCE: 34

Met Met Gln His Gln Val Asn Val Ser Ala Arg Phe Asn Pro Glu Thr
1               5                  10                  15

Leu Glu Arg Val Leu Arg Val Val Arg His Arg Gly Phe His Val Cys
            20                  25                  30

Ser Met Asn Met Ala Ala Ala Ser Asp Ala Gln Asn Ile Asn Ile Glu
        35                  40                  45

Leu Thr Val Ala Ser Pro Arg Ser Val Asp Leu Leu Phe Ser Gln Leu
    50                  55                  60

Asn Lys Leu Val Asp Val Ala His Val Ala Ile Cys Gln Ser Thr Thr
65                  70                  75                  80

Thr Ser Gln Gln Ile Arg Ala
                85
```